United States Patent [19]

Fowler et al.

[11] Patent Number: 6,103,464
[45] Date of Patent: Aug. 15, 2000

[54] METHOD OF DETECTING DNA ENCODING A β-GLUCOSIDASE FROM A FILAMENTOUS FUNGUS

[75] Inventors: Timothy Fowler, Belmont; Christopher C. Barnett, South San Francisco; Sharon Shoemaker, Fairfield, all of Calif.

[73] Assignee: Genencor International, Inc., Rochester, N.Y.

[21] Appl. No.: 08/463,461

[22] Filed: Jun. 5, 1995

Related U.S. Application Data

[62] Division of application No. 08/248,586, May 24, 1994, abandoned, which is a continuation of application No. 07/807,028, Dec. 10, 1991, abandoned, which is a continuation-in-part of application No. 07/625,140, Dec. 10, 1990, abandoned.

[51] Int. Cl.$^7$ .............................. C12Q 1/68; C07H 21/04
[52] U.S. Cl. .......................... 435/6; 536/23.1; 536/24.32
[58] Field of Search ...................... 435/6, 253; 536/23.1, 536/24.32

[56] References Cited

U.S. PATENT DOCUMENTS

| | | | |
|---|---|---|---|
| 4,275,163 | 6/1981 | Gallo | 435/209 |
| 4,745,062 | 5/1988 | Guerineau et al. | 435/209 |
| 4,885,252 | 12/1989 | Ingolia et al. | 435/209 |
| 4,892,819 | 1/1990 | Carr et al. | 435/69.1 |
| 4,935,349 | 6/1990 | McKnight et al. | 435/69.5 |

FOREIGN PATENT DOCUMENTS

| | | |
|---|---|---|
| 148 668 | 7/1985 | European Pat. Off. . |
| 263571 | 1/1989 | Germany . |
| 63-226294 | 9/1988 | Japan . |
| 5-115293 | 5/1993 | Japan . |
| 90/00192 | 1/1990 | WIPO . |
| 91/17244 | 11/1991 | WIPO . |
| 92/06209 | 4/1992 | WIPO . |
| 92/06210 | 4/1992 | WIPO . |

OTHER PUBLICATIONS

Barnett C., et al., "Expression of *Trichoderma reesei* exo-cellobiohydrolase II genes in *Asperigillus awamori*: a heterologous expression system to study structure–function relationships—enzyme engineering applications", Abstr. Pap. Am. Chem. Soc., 195 Meeting (1988) (Abstract).

Bause et al., "Isolation and Structure of a Tryptic Glyucopeptide from the Active Site of β–glucosidase A$_3$ From *Aspergillus wentil*" Biochim Biophys. Acta 626:459–465 (1980).

Bause et al., "Isolation and amino–acid sequence of a hexa deca peptide from the active site of beta–glucosidase A–3 from *Aspergillus wentil*", Hoope–Seyler's Physiol. Chem. 355(4), pp. 438–442 (1974).

Berka, et al., "Cloning of a Themostable Clucoamylase from the Thermophilic Fungus *Humnicola Grisea* and its expression in *Aspergillus niger*" NDC Finland Conference (Jun. 1989).

Bhikhabhai, P., et al., "Isolation of cellulolytic enzymes from *Trichoderma reesei*", J. Applied Biochemistry 6:336–345 (1984).

Bisaria et al., "Regulatory aspects of cellulase biosynthesis and secretion beta–glucosidase protein secretion, review" Crit. Rev. Biotechnol. 9(2):61–103 (1989) (Abstract).

Chen, et al., "Purification and characterization of two extracellular β–glucosidases from *Trichoderma reesei*" Biochem et Biophysica Acta 1121:54–60 (1992).

Chirico, et al., "Purification and characterization of a β–glucosidase from *Trichoderma reesei*" Eur. J. Biochem. 165:333–341 (1987).

Durand, H., et al., "Classical and molecular genetics applied to *Trichoderma reesei* for the selection of improved cellulolytic industrial strains—beta–glucosidase and cellulase activity; beta–D–fructofuranosidase gene cloning and expression in *Trichoderma reesei*; cellulose degradation", FEMS Symp. vol. 43 (1988) (Abstract).

Finkelstein, D., "Transformation" *The Biotechnology of Filamentous Fungi*, pp. 113–156, Eds, D.B. Finkelstein and C. Ball, , Boston, Butterworth–Heinemann, 1992.

Fowler, et al., "Developments in recombinant beta–glucosidase of *Trichoderma reesei*—cellulase complex recombinant beta–glucosidase production" Abstr. Pap. Am. Chem. Soc., 202 Meeting, Abstr. No. 91–14368 (1991) (Abstract).

Glick, B.R., et al., "Isolation, characterization, and manipulation of cellulase genes: cellobiohydrolase and beta–glucosidase genes cloning and expression; cellulase complex; a review", Biotechnol. Adv. 7(3):361–386.

Gritzali, M. "Enzymes of the cellulase system of Trichoderma: an overview—cellulase complex characterization", Abstr. Pap. Am. Chem. Soc., 194 Meeting (1987) (Abstract).

Gwynne et al., "Genetically Engineered Secretion of Active Human Interferon and a Bacterial Endoglucanase from *Aspergillus nidulans*" Bioctechnology 5:713–719 (Jul. 1987).

Harkki, et al., "Genetic engineering of Trichoderma to produce strains with novel cellulase profiles" Enzyme Microb. Techol. 13:227–233 (Mar. 1991).

Harkki et al., "A novel fungal expression system:Secretion of Active Calf Chymosin from the Filamentous Fungus *Trichoderma reesi*" Biotechnology 7:596–603 (Jun. 1989).

Hofer, et al., "A Monoclonal Antibody Against the Alkaline Extracellular Beta Glucosidase from *Trichderma reesei* reactivity with other Trichoderma Beta Blucosidases" et al., Biochem. Bioplhys Acta 992 (3):298–306 (1989) (Abstract).

(List continued on next page.)

Primary Examiner—W. Gary Jones
Assistant Examiner—Amy Atzel
Attorney, Agent, or Firm—Christopher L. Stone

[57] ABSTRACT

A process for expressing extracellular β-glucosidase in a filamentous fungus by expressing a fungal DNA sequence encoding enhanced, deleted or altered β-glucosidase in a recombinant host microorganism is disclosed. Recombinant fungal cellulase compositions containing enhanced, deleted or altered expression of β-glucosidase is also disclosed.

3 Claims, 13 Drawing Sheets

OTHER PUBLICATIONS

Kalra, M.K., et al., "Partial purification, characterization, and regulation of cellulolytic enzymes from *Trichoderma longibrachiatum*", *J. Applied Bacteriology* 61:73–80 (1986).

Kawamori, M., et al., "Preparation and application of *Trichoderma reesei* mutants with enhanced beta–glucosidase" *Agric. Biol. Chem.* 50(10):2477–2482 (1986).

Knowles, J., et al., "The cloning of fungal cellulase genes and their expression in yeast: cellobiohydrolase and beta–glucosidase gene expression in transformed *Saccharomyces cerevisiae*", FEBS Congress 16th Meeting, Part C, pp. 43–49 (1985) (Abstract).

Knowles, J., "Applications of the molecular biology of *Trichoderma reesei*", Proceedings of the EMBO–Alko Workshop on Molecular Biology of Filamentous Fungi, Helsinki 1989, ed. by H. Nevalainen and M. Penttila pp. 113–118.

Knowles, J., et al., "The use of gene technology to investigate fungal cellulolytic enzymes—*Trichoderma reesei* cellulase complex gene cloning and expression in *Saccharomyces cerevisiae*", FEMS Symp. vol. 43 (1988) (Abstract).

Maniatis et al., *Molecular Cloning: A Laboratory Manual* Cold Springs Harbor 226, 227, 228 and 432 (1982).

Merivuori, et al., "Regulation of cellulase biosynthesis and secretion in fungi—*Trichoderma reesei*" *Biochem. Soc. Trans.* 13(2):411–414 (1985).

Merivuori, et al., "Effects of alcohol and temperature on secretion by Trichoderma—cellulase complex production by Trichoderma reesei" *Trichoderma reesei Cellulases*, pp. 103–114 (1990).

Meyer, et al., "The use of DNA–fingerprint analysis in the classification of some species of the Trichoderma aggregate" *Current Genetics* 21:27–30 (1992).

Mishra, et al., "Isolation and Characterization of A Mutant of *Trichoderma reesei* Showing Reduced Levels of Extracellular β–Glucosidase" *J. Gen. Microbiol.* 135:3459–3465 (1989).

Nevalainen et al., "The Molecular Biology of Trichoderma and Its Application to the Expression of Both Homologous and Heterologous Genes" Molecular industrial mycoloyg: systems and applications for filamentous fungi, pp. 129–148, eds. Sally A. Leong, New York, Marcel Dekker, Inc. 1991.

Ong, et al., "The Cellulose binding domains of cellulases: tools for biotechnology application in protein or fusion protein purification by affinity chromatography and in enzyme immobilization, a review" *Biotechnology* 7(9):239–241 (1989) (Abstract).

Ong et al., "Enzyme immobilization or purifcation using the cellulose–binding domains of the two bacterial cellulases", *Protein Engn.* 3(4):379 (1990).

Penttila, M.E., et al., "Construction of brewer's yeast secreting fungal endo–beta–glucanase" *Current Genetics* 12:413–420 (1987).

Penttila, M.E., et al., "Cloning of *Aspergillus niger* genes in yeast. Expression of the gene coding Aspergillus beta–glucosidase", *Molecular General Genetics*, 194:494–499 (1984).

Penttila et al., "A veratile tranformation system for the celluloytic filametous fungus *Trichoderma reesei*" *Gene* 61:155–164 (1987).

Pouwels et al., *Cloning Vectors* Elsevier Science Publishers B.V., pp. ppv–A–i–1, V–A–ii–1 (1984).

Raynal, A., et al., "Sequence and transcription of the beta–glucosidase gene of *Kluyvermyces fragilis* in *Saccharomyces cerevisiae*", *Current Genetics* 12:175–184 (1987).

Rickard, P., et al., "Kinetic properties and contribution to cellulose saccharification of a cloned Pseudomonas beta–glucosidase: enzyme cloning using plasmid pND71 and use of recombinant product in association with *Trichoderman reesei* cellulase", *Aust. J. Biotechnol.* 3(1):43–49 (1989).

Sahasrabudhe e al., Genome complexity of a powerful celluloytic fungus, *Penicillium funiculosum FEBS Microbiology Ltrs.* 30:295–300 (1985).

Shoemaker, S.P., et al., "The cellulase system of *Trichoderma reesei*: Trichoderma strain improvement and expression of Trichoderma cellulase in yeast—in ethanol production", World Biotech. Rep. vol. 2, pp. 593–600 (1984).

Smith, et al., "Sequence of the cloned pyr4 gene of *Trichoderma reesei* and its use as a homologous slectable marker for tranformation" *Curr. Genet.* 19–33 (1991).

Strauss, J. and Kubicek, C.P. "Beta–glucosidase and cellulase formation by a *Trichoderma reesei* mutant defective in constitutive beta–glucosidase formation", *J. Gen. Microbiol.* 136:1321–1326 (1990).

van Hartingsveldt, et al., "Development of a homologous transformation system for *aspergillus niger* based on the pyrG gene" *Mol. Gen. Genet* 206:71–75 (1987).

Wakarchuk, W.W., et al., "Structure and transcription anaylsis of the gene encoding a cellobiose from Agrobacterium sp. strain ATCC 21400", *J. Bacteriology* 170(1), pp. 301–307 (1988).

Wang, et al., An efficient approach for the preparation of fungal protoplasts: protoplast formations and regeneration in *Trichoderma kiningii*, *Proc. Nat. Sci. Coun. Repub. of China Part B life science*:12(2):69–76 (1988) (Abstract).

Wilson, et al., "Sequence of the *aspergillus nigher* pyrG gene" *Nucleic Acids Research* 16(5):2339 (1988).

Yelton, M.M., et al., "A cosmid for selecting genes by complementation in *Aspergillus nidulans*: selection of the developmentally regulated yA locus", *PNAS:USA* 82:834–838 (1985).

Young, et al., "Efficient isolation of genes by using antibody probes" *PNAS* 80:1194–1198 (1983).

```
TGGCCACAGA GGGAGAGTTC GCGCTACCGC TTGGTCGAGG AAATGATCGC CCACGGCCTC     60

AAATCGTAAA TCTCGGTGTG GGTAGGAGTG CAACGATGGG ATTTGGCCGC AATGCTGCCG    120

AGCCCGAGTG TTTCTGCAAC GTTATCCAGG AGATTTGCGC TTGCCCAAGA GGGAGTTGAC    180

GGGGAGAGTC CCAACTGGTT CCTTCAGTAA CGCCACCCTG GCAGACTATA TAACTTGTGG    240

ACAAGACTCT GCTTTGTTGA GTTCTTCCTA CCAGTCTTGA CCAAGACCAT TCTGTTGAGC    300
```

```
CCAATCAGAA ATG CGT TAC CGA ACA GCA GCT GCG CTG GCA CTT GCC ACT       349
           Met Arg Tyr Arg Thr Ala Ala Ala Leu Ala Leu Ala Thr
            1           5                  10
```

```
GGG CCC TTT GCT AGG GCA GAC AGT  CA  GTATAGCTGG TCCATACTGG          395
Gly Pro Phe Ala Arg Ala Asp Ser His
    15                  20
```

```
GATGTGATAT GTATCCTGGA GACACCATGC TGACTCTTGA ATCAAGGTAG C TCA ACA    452
                                                        Ser Thr
```

```
TCG GGG GCC TCG GCT GAG GCA GTT GTA CCT CCT GCA GGG ACT CCA TGG      500
Ser Gly Ala Ser Ala Glu Ala Val Val Pro Pro Ala Gly Thr Pro Trp
 25          30                  35                  40

GGA ACC GCG TAC GAC AAG GCG AAG GCC GCA TTG GCA AAG CTC AAT CTC      548
Gly Thr Ala Tyr Asp Lys Ala Lys Ala Ala Leu Ala Lys Leu Asn Leu
                 45                  50                  55

CAA GAT AAG GTC GGC ATC GTG AGC GGT GTC GGC TGG AAC GGC GGT CCT      596
Gln Asp Lys Val Gly Ile Val Ser Gly Val Gly Trp Asn Gly Gly Pro
         60                  65                  70

TGC GTT GGA AAC ACA TCT CCG GCC TCC AAG ATC AGC TAT CCA TCG CTA      644
Cys Val Gly Asn Thr Ser Pro Ala Ser Lys Ile Ser Tyr Pro Ser Leu
         75                  80                  85

TGC CTT CAA GAC GGA CCC CTC GGT GTT CGA TAC TCG ACA GGC AGC ACA      692
Cys Leu Gln Asp Gly Pro Leu Gly Val Arg Tyr Ser Thr Gly Ser Thr
         90                  95                 100

GCC TTT ACG CCG GGC GTT CAA GCG GCC TCG ACG TGG GAT GTC AAT TTG      740
Ala Phe Thr Pro Gly Val Gln Ala Ala Ser Thr Trp Asp Val Asn Leu
105                 110                 115                 120

ATC CGC GAA CGT GGA CAG TTC ATC GGT GAG GAG GTG AAG GCC TCG GGG      788
Ile Arg Glu Arg Gly Gln Phe Ile Gly Glu Glu Val Lys Ala Ser Gly
                125                 130                 135

ATT CAT GTC ATA CTT GGT CCT GTG GCT GGG CCG CTG GGA AAG ACT CCG      836
Ile His Val Ile Leu Gly Pro Val Ala Gly Pro Leu Gly Lys Thr Pro
            140                 145                 150
```

FIG._1A

```
CAG GGC GGT CGC AAC TGG GAG GGC TTC GGT GTC GAT CCA TAT CTC ACG      884
Gln Gly Gly Arg Asn Trp Glu Gly Phe Gly Val Asp Pro Tyr Leu Thr
        155                 160                 165

GGC ATT GCC ATG GGT CAA ACC ATC AAC GGC ATC CAG TCG GTA GGC GTG      932
Gly Ile Ala Met Gly Gln Thr Ile Asn Gly Ile Gln Ser Val Gly Val
170                 175                 180

CAG GCG ACA GCG AAG CAC TAT ATC CTC AAC GAG CAG GAG CTC AAT CGA      980
Gln Ala Thr Ala Lys His Tyr Ile Leu Asn Glu Gln Glu Leu Asn Arg
185                 190                 195                 200

GAA ACC ATT TCG AGC AAC CCA GAT GAC CGA ACT CTC CAT GAG CTG TAT     1028
Glu Thr Ile Ser Ser Asn Pro Asp Asp Arg Thr Leu His Glu Leu Tyr
                205                 210                 215

ACT TGG CCA TTT GCC GAC GCG GTT CAG GCC AAT GTC GCT TCT GTC ATG     1076
Thr Trp Pro Phe Ala Asp Ala Val Gln Ala Asn Val Ala Ser Val Met
                220                 225                 230

TGC TCG TAC AAC AAG GTC AAT ACC ACC TGG GCC TGC GAG GAT CAG TAC     1124
Cys Ser Tyr Asn Lys Val Asn Thr Thr Trp Ala Cys Glu Asp Gln Tyr
        235                 240                 245

ACG CTG CAG ACT GTG CTG AAA GAC CAG CTG GGG TTC CCA GGC TAT GTC     1172
Thr Leu Gln Thr Val Leu Lys Asp Gln Leu Gly Phe Pro Gly Tyr Val
250                 255                 260

ATG ACG GAC TGG AAC GCA CAG CAC ACG ACT GTC CAA AGC GCG AAT TCT     1220
Met Thr Asp Trp Asn Ala Gln His Thr Thr Val Gln Ser Ala Asn Ser
265                 270                 275                 280

GGG CTT GAC ATG TCA ATG CCT GGC ACA GAC TTC AAC GGT AAC AAT CGG     1268
Gly Leu Asp Met Ser Met Pro Gly Thr Asp Phe Asn Gly Asn Asn Arg
                285                 290                 295

CTC TGG GGT CCA GCT CTC ACC AAT GCG GTA AAT AGC AAT CAG GTC CCC     1316
Leu Trp Gly Pro Ala Leu Thr Asn Ala Val Asn Ser Asn Gln Val Pro
                300                 305                 310

ACG AGC AGA GTC GAC GAT ATG GTG ACT CGT ATC CTC GCC GCA TGG TAC     1364
Thr Ser Arg Val Asp Asp Met Val Thr Arg Ile Leu Ala Ala Trp Tyr
                315                 320                 325

TTG ACA GGC CAG GAC CAG GCA GGC TAT CCG TCG TTC AAC ATC AGC AGA     1412
Leu Thr Gly Gln Asp Gln Ala Gly Tyr Pro Ser Phe Asn Ile Ser Arg
        330                 335                 340

AAT GTT CAA GGA AAC CAC AAG ACC AAT GTC AGG GCA ATT GCC AGG GAC     1460
Asn Val Gln Gly Asn His Lys Thr Asn Val Arg Ala Ile Ala Arg Asp
345                 350                 355                 360

GGC ATC GTT CTG CTC AAG AAT GAC GCC AAC ATC CTG CCG CTC AAG AAG     1508
Gly Ile Val Leu Leu Lys Asn Asp Ala Asn Ile Leu Pro Leu Lys Lys
                365                 370                 375
```

FIG.—1B

```
CCC GCT AGC ATT GCC GTC GTT GGA TCT GCC GCA ATC ATT GGT AAC CAC    1556
Pro Ala Ser Ile Ala Val Val Gly Ser Ala Ala Ile Ile Gly Asn His
            380             385             390

GCC AGA AAC TCG CCC TCG TGC AAC GAC AAA GGC TGC GAC GAC GGG GCC    1604
Ala Arg Asn Ser Pro Ser Cys Asn Asp Lys Gly Cys Asp Asp Gly Ala
            395             400             405

TTG GGC ATG GGT TGG GGT TCC GGC GCC GTC AAC TAT CCG TAC TTC GTC    1652
Leu Gly Met Gly Trp Gly Ser Gly Ala Val Asn Tyr Pro Tyr Phe Val
            410             415             420

GCG CCC TAC GAT GCC ATC AAT ACC AGA GCG TCT TCG CAG GGC ACC CAG    1700
Ala Pro Tyr Asp Ala Ile Asn Thr Arg Ala Ser Ser Gln Gly Thr Gln
425             430             435             440

GTT ACC TTG AGC AAC ACC GAC AAC ACG TCC TCA GGC GCA TCT GCA GCA    1748
Val Thr Leu Ser Asn Thr Asp Asn Thr Ser Ser Gly Ala Ser Ala Ala
            445             450             455

AGA GGA AAG GAC GTC GCC ATC GTC TTC ATC ACC GCC GAC TCG GGT GAA    1796
Arg Gly Lys Asp Val Ala Ile Val Phe Ile Thr Ala Asp Ser Gly Glu
            460             465             470

GGC TAC ATC ACC GTG GAG GGC AAC GCG GGC GAT CGC AAC AAC CTG GAT    1844
Gly Tyr Ile Thr Val Glu Gly Asn Ala Gly Asp Arg Asn Asn Leu Asp
            475             480             485

CCG TGG CAC AAC GGC AAT GCC CTG GTC CAG GCG GTG GCC GGT GCC AAC    1892
Pro Trp His Asn Gly Asn Ala Leu Val Gln Ala Val Ala Gly Ala Asn
            490             495             500

AGC AAC GTC ATT GTT GTT GTC CAC TCC GTT GGC GCC ATC ATT CTG GAG    1940
Ser Asn Val Ile Val Val Val His Ser Val Gly Ala Ile Ile Leu Glu
505             510             515             520

CAG ATT CTT GCT CTT CCG CAG GTC AAG GCC GTT GTC TGG GCG GGT CTT    1988
Gln Ile Leu Ala Leu Pro Gln Val Lys Ala Val Val Trp Ala Gly Leu
            525             530             535

CCT TCT CAG GAG AGC GGC AAT GCG CTC GTC GAC GTG CTG TGG GGA GAT    2036
Pro Ser Gln Glu Ser Gly Asn Ala Leu Val Asp Val Leu Trp Gly Asp
            540             545             550

GTC AGC CCT TCT GGC AAG CTG GTG TAC ACC ATT GCG AAG AGC CCC AAT    2084
Val Ser Pro Ser Gly Lys Leu Val Tyr Thr Ile Ala Lys Ser Pro Asn
            555             560             565

GAC TAT AAC ACT CGC ATC GTT TCC GGC GGC AGT GAC AGC TTC AGC GAG    2132
Asp Tyr Asn Thr Arg Ile Val Ser Gly Gly Ser Asp Ser Phe Ser Glu
            570             575             580

GGA CTG TTC ATC GAC TAT AAG CAC TTC GAC GAC GCC AAT ATC ACG CCG    2180
Gly Leu Phe Ile Asp Tyr Lys His Phe Asp Asp Ala Asn Ile Thr Pro
585             590             595             600
```

*FIG._1C*

```
CGG TAC GAG TTC GGC TAT GGA CTG  T GTAAGTTTGC TAACCTGAAC              2225
Arg Tyr Glu Phe Gly Tyr Gly Leu
                605

AATCTATTAG ACAGGTTGAC TGACGGATGA CTGTGGAATG ATAG  CT TAC ACC AAG      2280
                                                   Ser Tyr Thr Lys
                                                          610

TTC AAC TAC TCA CGC CTC TCC GTC TTG TCG ACC GCC AAG TCT GGT CCT       2328
Phe Asn Tyr Ser Arg Leu Ser Val Leu Ser Thr Ala Lys Ser Gly Pro
        615                 620                 625

GCG ACT GGG GCC GTT GTG CCG GGA GGC CCG AGT GAT CTG TTC CAG AAT       2376
Ala Thr Gly Ala Val Val Pro Gly Gly Pro Ser Asp Leu Phe Gln Asn
        630                 635                 640

GTC GCG ACA GTC ACC GTT GAC ATC GCA AAC TCT GGC CAA GTG ACT GGT       2424
Val Ala Thr Val Thr Val Asp Ile Ala Asn Ser Gly Gln Val Thr Gly
645                 650                 655                 660

GCC GAG GTA GCC CAG CTG TAC ATC ACC TAC CCA TCT TCA GCA CCC AGG       2472
Ala Glu Val Ala Gln Leu Tyr Ile Thr Tyr Pro Ser Ser Ala Pro Arg
                665                 670                 675

ACC CCT CCG AAG CAG CTG CGA GGC TTT GCC AAG CTG AAC CTC ACG CCT       2520
Thr Pro Pro Lys Gln Leu Arg Gly Phe Ala Lys Leu Asn Leu Thr Pro
                680                 685                 690

GGT CAG AGC GGA ACA GCA ACG TTC AAC ATC CGA CGA CGA GAT CTC AGC       2568
Gly Gln Ser Gly Thr Ala Thr Phe Asn Ile Arg Arg Arg Asp Leu Ser
                695                 700                 705

TAC TGG GAC ACG GCT TCG CAG AAA TGG GTG GTG CCG TCG GGG TCG TTT       2616
Tyr Trp Asp Thr Ala Ser Gln Lys Trp Val Val Pro Ser Gly Ser Phe
        710                 715                 720

GGC ATC AGC GTG GGA GCG AGC AGC CGG GAT ATC AGG CTG ACG AGC ACT       2664
Gly Ile Ser Val Gly Ala Ser Ser Arg Asp Ile Arg Leu Thr Ser Thr
725                 730                 735                 740

CTG TCG GTA GCG TAGCGCGAGG AGGGTGAAGG CGGTTGACCT GTGACTGTGA           2716
Leu Ser Val Ala
                745

GTGAGGACCG AAGGTGGGAT GGCGTGAATA CTGCAGGAAT ACAATCTTCA GGATAGGCAT    2776

CAGAGCAGTA ACATGAATGA TGAAGACGGC CGAAGCAGAA GTGAATTGAG GAGGTAGTGA    2836

TGATGAAATG TGAGGGAAGA GAGATGTTCA ATCACCTTGT TCGAGGGAAG CTGCAAATTG    2896

GGCCTCACGT CATCTCGCAG AGAGAAGGAA CTCTTGCAGC AGGAGTTCTG CTCACTGAGA    2956

AGAAGGCCCG GGTTAGCGTC GCGCCTCTTC CGCGACATCC TCCGCTCCGG CACTGTGCTG    3016

TCAAACTGGC ACCAACA                                                    3033
```

FIG._1D

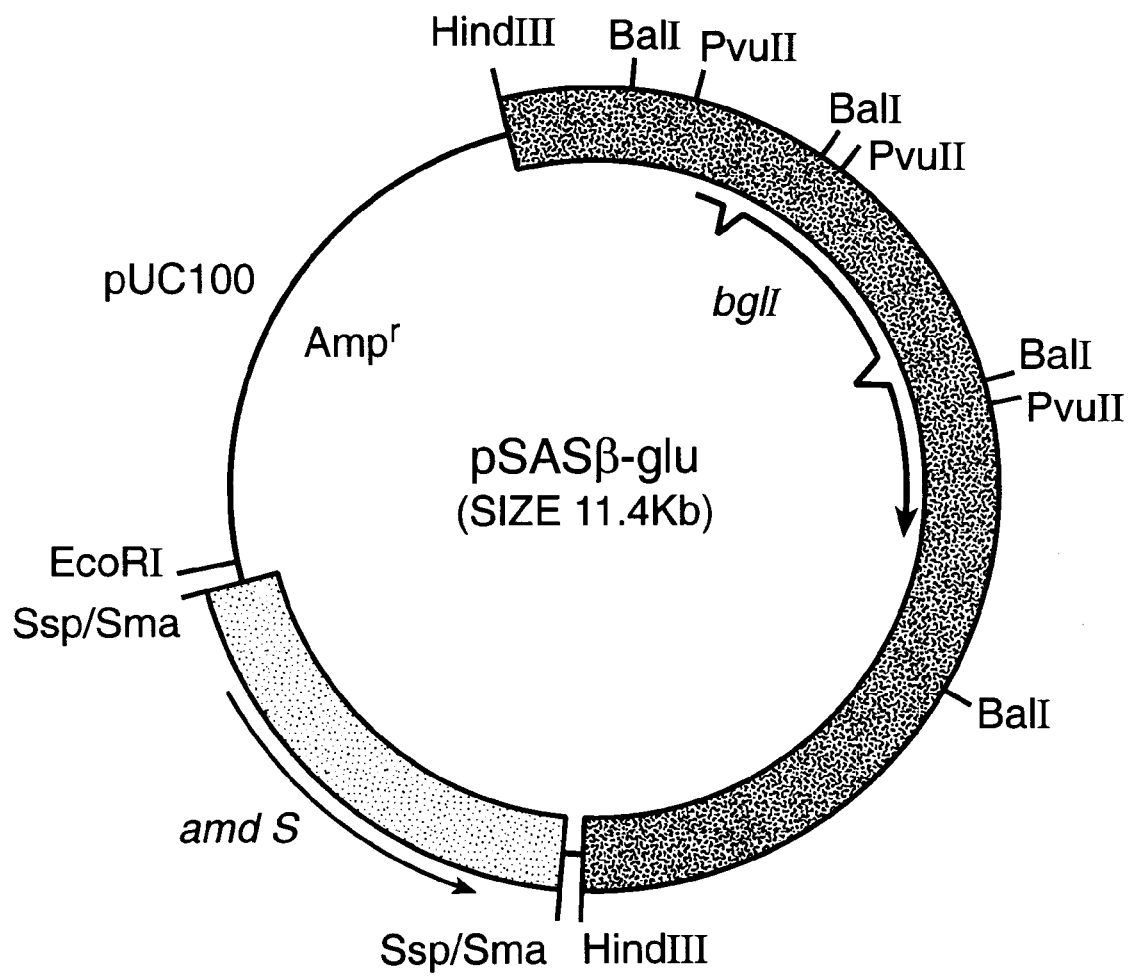
FIG._2

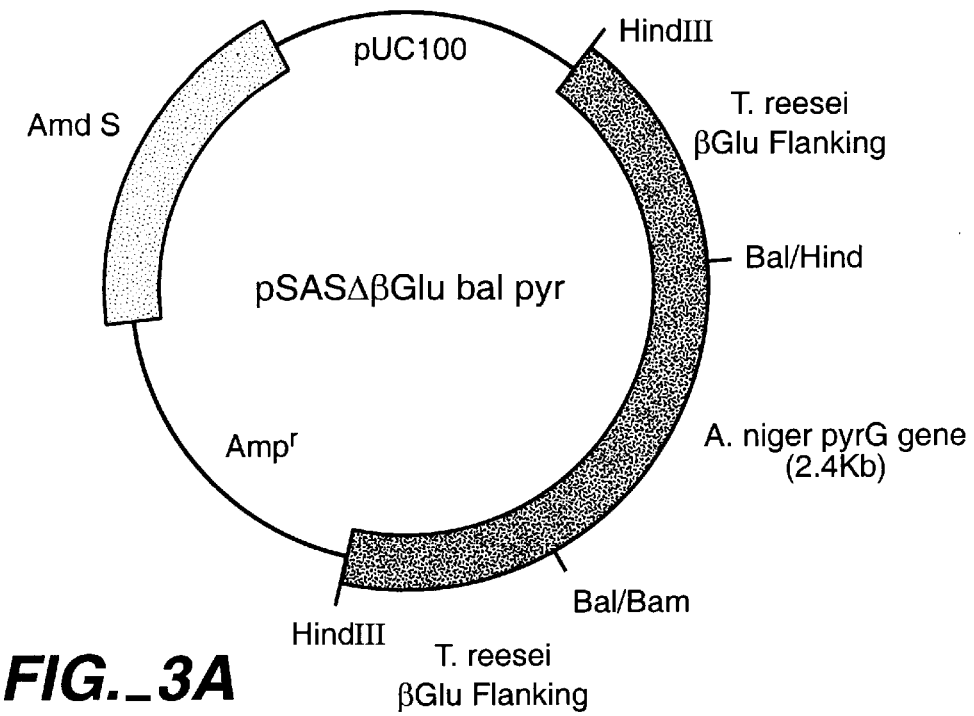
FIG._3A
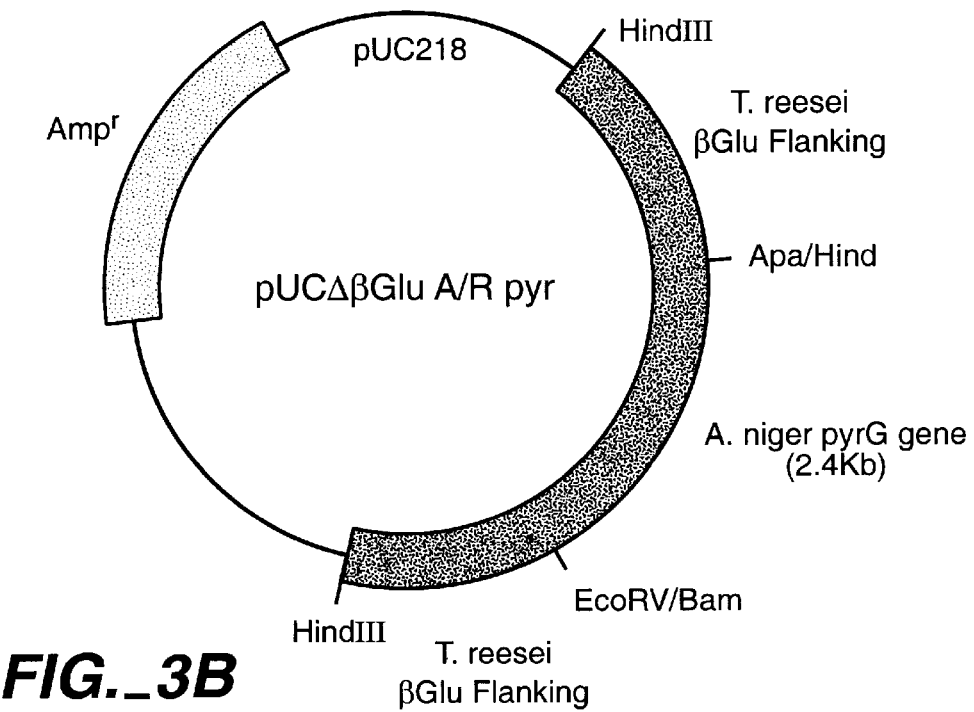
FIG._3B

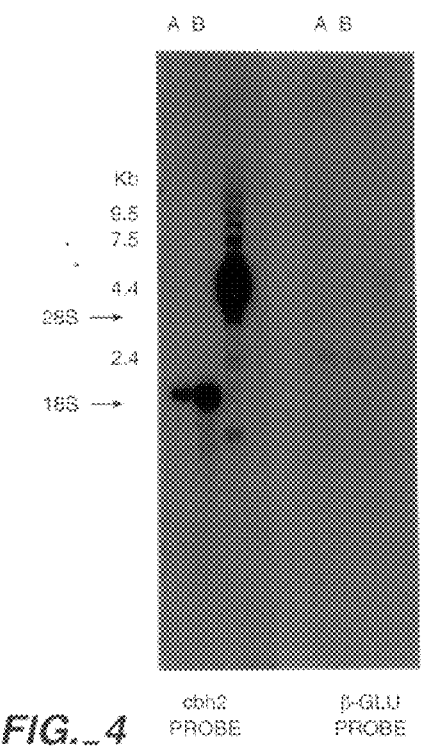
FIG._4
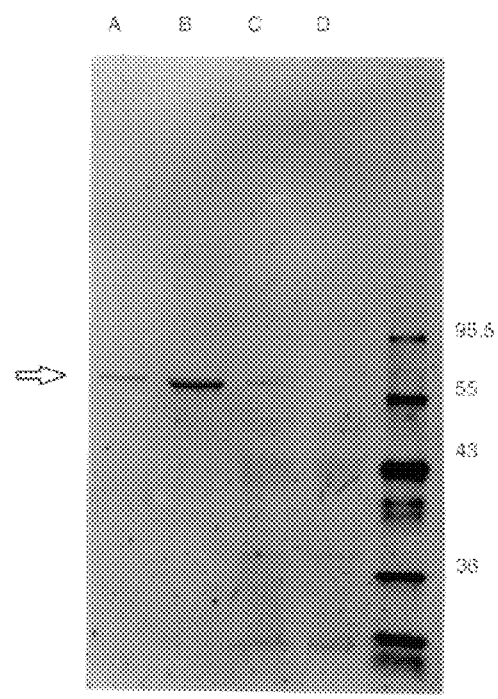
FIG._5C

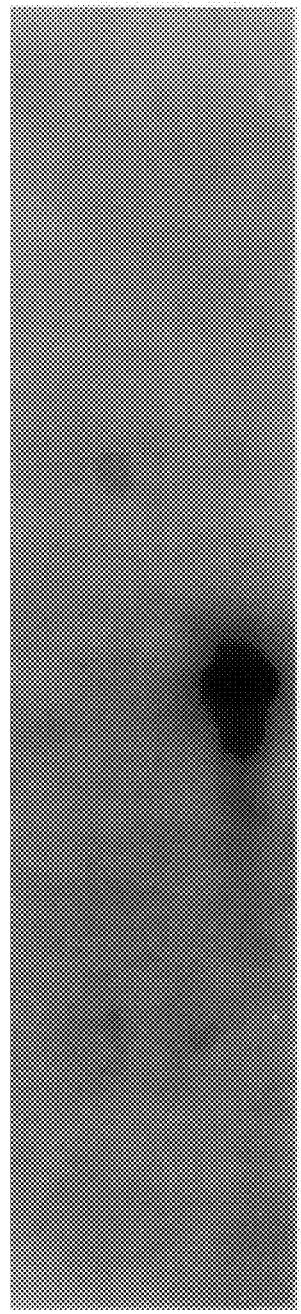
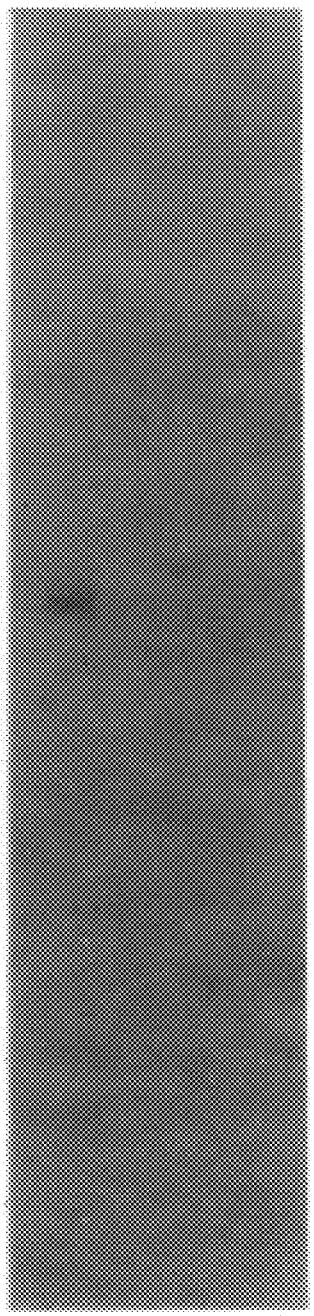
*FIG._5A*  *FIG._5B*

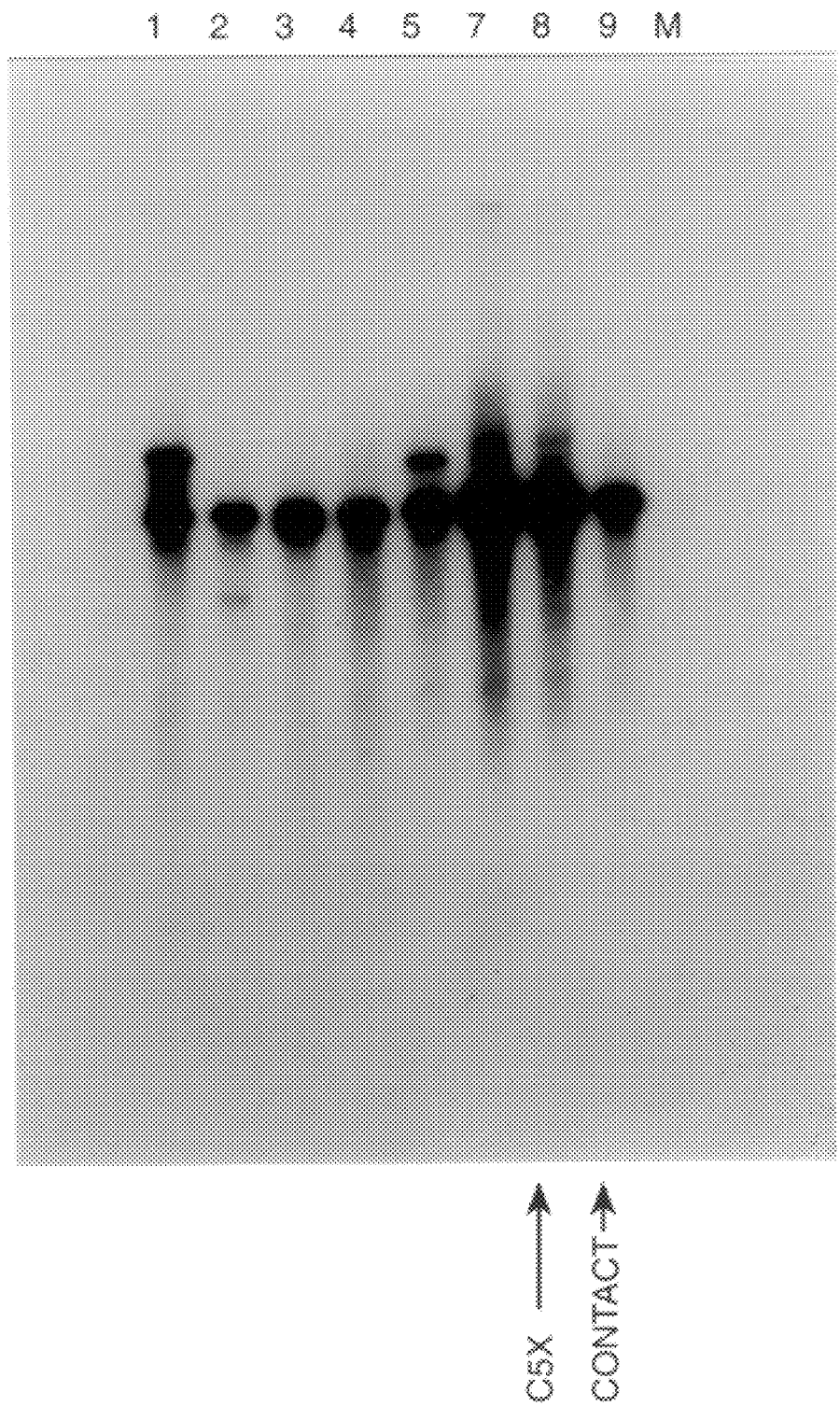
FIG._6

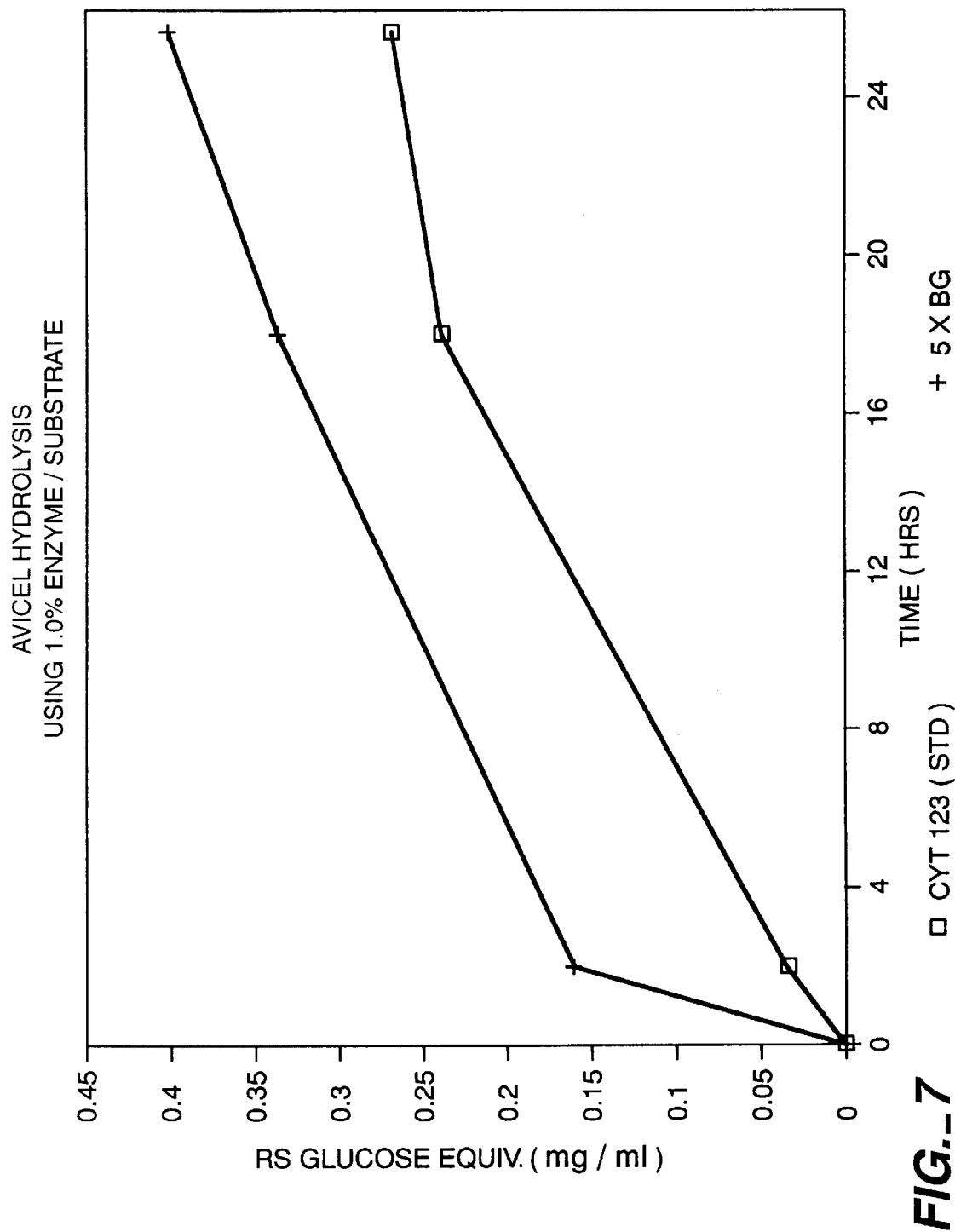
FIG._7

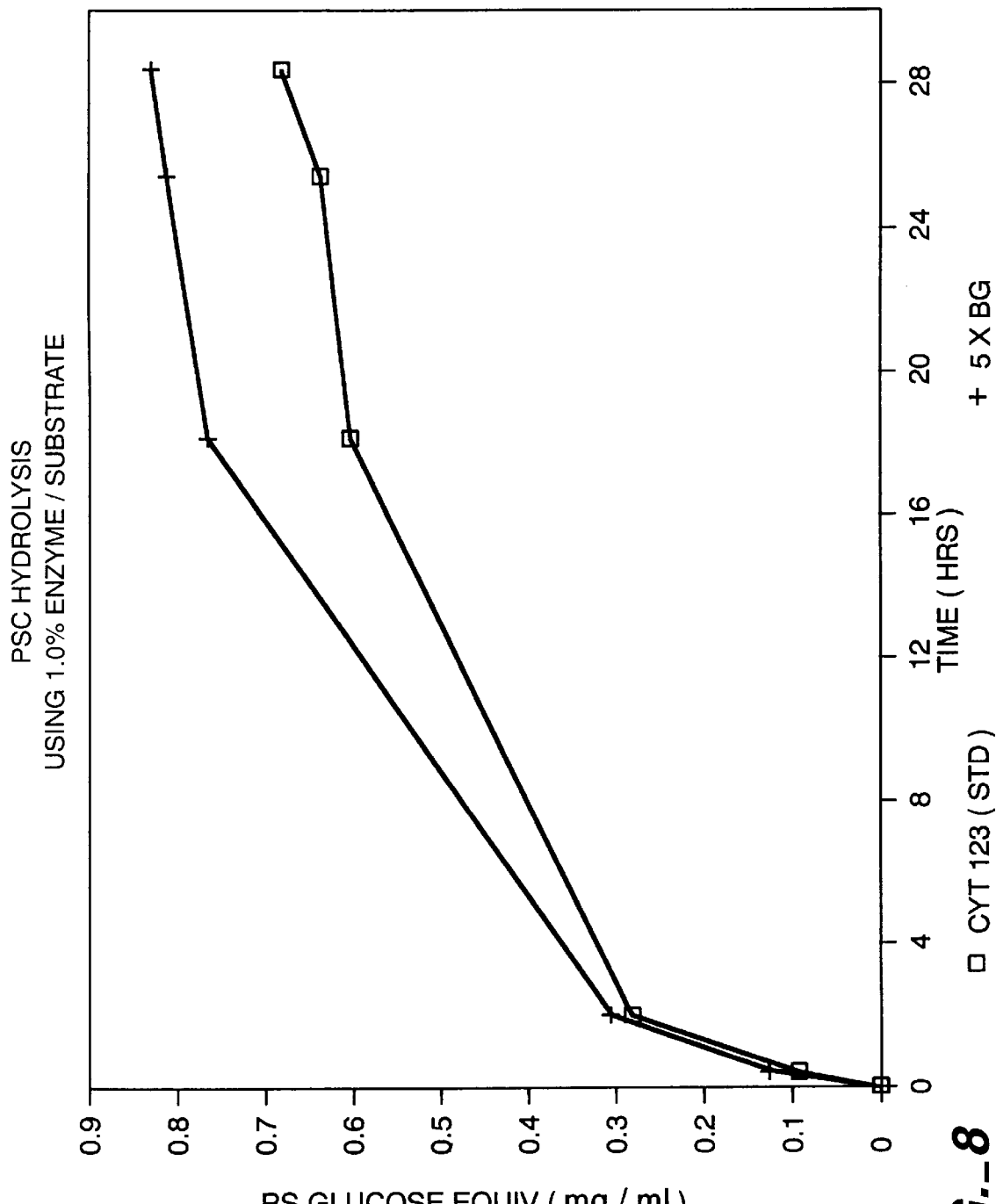
FIG._8

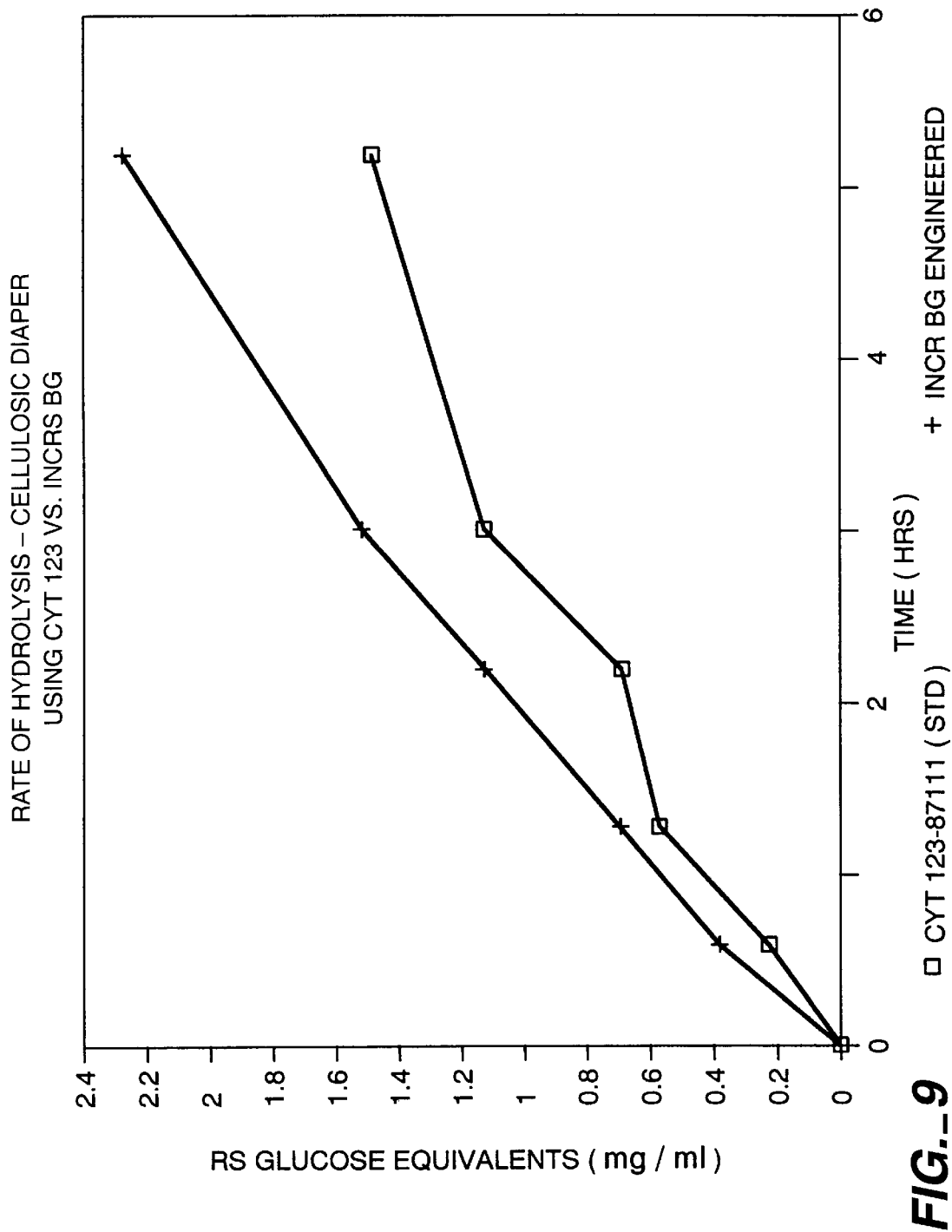
FIG._9

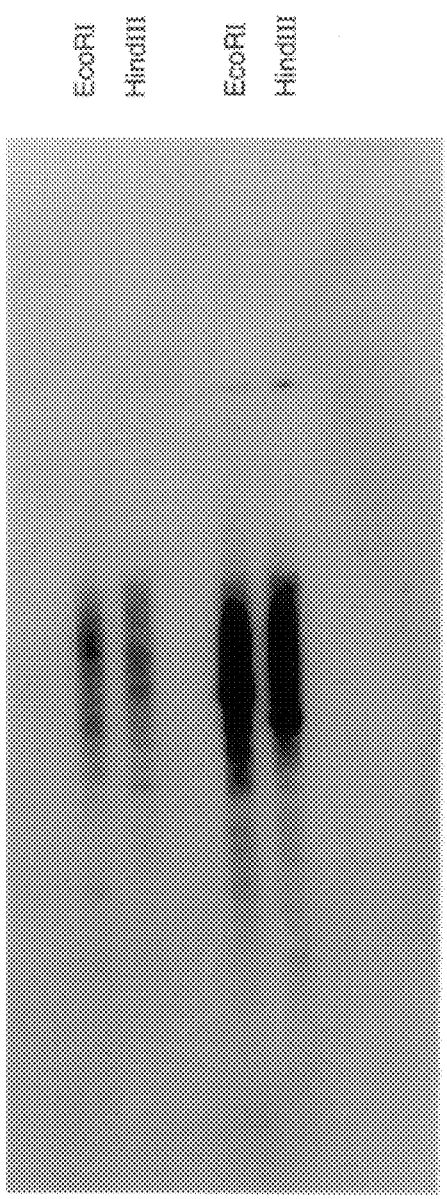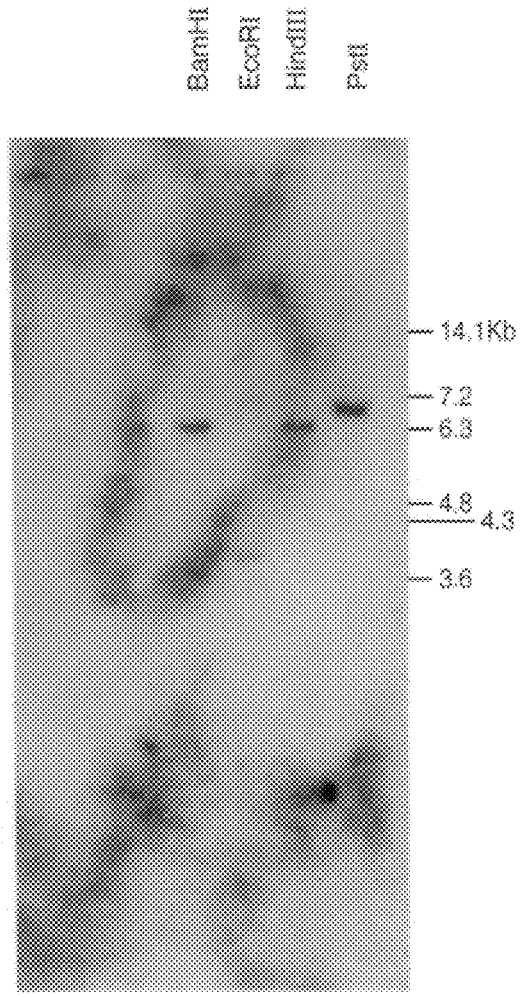
Humicula grisea
FIG._10B
A. nidulans  N. crassa
FIG._10A

METHOD OF DETECTING DNA ENCODING A β-GLUCOSIDASE FROM A FILAMENTOUS FUNGUS

This is a Divisonal of U.S. Ser. No. 08/248,586 filed May 24, 1994, now abandoned, which is a continuation application of 07/807,028 filed Dec. 10, 1991, now abandoned, which is a continuation-in-part of 07/625,140 filed Dec. 10, 1990, now abandoned.

BACKGROUND OF THE INVENTION

1. Field of the Invention

The present invention relates to cellulase preparations and compositions having increased or decreased cellulolytic capacity. The invention further relates to a nucleotide sequence of the bg11 gene encoding extracellular β-glucosidase from a filamentous fungi, a plasmid vector containing the gene encoding extracellular β-glucosidase and transformant strains with increased copy numbers of the β-glucosidase (bg11) gene introduced into the genome. More particularly, the present invention relates to Trichoderma reesei strains that have increased or no levels of expression of the bg11 gene resulting in enhanced or no extracellular β-glucosidase protein levels that can be used in conjunction with other compositions to produce a cellulase product having increased or decreased cellulolytic capacity.

2. State of the Art

Cellulases are known in the art as enzymes that hydrolyze cellulose (β-1,4-glucan linkages), thereby resulting in the formation of glucose, cellobiose, cellooligosaccharides, and the like. As noted by Wood et al., "Methods in Enzymology", 160, 25, pages 234 et seq. (1988) and elsewhere, cellulase produced by a given microorganism is comprised of several different enzyme classes including those identified as exocello-biohydrolases (EC 3.2.1.91) ("CBH"), endoglucanases (EC 3.2.1.4) ("EG"), β-glucosidases (EC 3.2.1.21) ("BG"). Moreover, the fungal classifications of CBH, EG and BG can be further expanded to include multiple components within each classification. For example, multiple CBHs and EGs have been isolated from a variety of bacterial and fungal sources including Trichoderma reesei which contains 2 CBHs, i.e., CBH I and CBH II, and at least 3 EGs, i.e., EG I, EG II, and EG III components.

The complete cellulase system comprising components from each of the CBH, EG, and BG classifications is required to efficiently convert crystalline forms of cellulose to glucose. Isolated components are far less effective, if at all, in hydrolyzing crystalline cellulose. Moreover, a synergistic relationship is observed between the cellulase components particularly if they are of different classifications. That is to say, the effectiveness of the complete cellulase system is significantly greater than the sum of the contributions from the isolated components of the same classification. In this regard, it is known in the art that the EG components and CBH components synergistic- ally interact to more efficiently degrade cellulose. See, for example, Wood, Biochem. Soc. Trans., 13, pp. 407–410 (1985).

The substrate specificity and mode of action of the different cellulase components varies with classification, which may account for the synergy of the combined components. For example, the current accepted mode of cellulase action is that endoglucanase components hydrolyze internal β-1,4-glucosidic bonds, particularly, in regions of low crystallinity of the cellulose and exo-cellobiohydrolase components hydrolyze cellobiose from the non-reducing end of cellulose. The action of endoglucanase components greatly facilitates the action of exo-cellobiohydrolases by creating new chain ends which are recognized by exo-cellobiohydrolase components.

β-Glucosidases are essential components of the cellulase system and are important in the complete enzymatic breakdown of cellulose to glucose. The β-glucosidase enzymes can catalyze the hydrolysis of alkyl and/or aryl β-D-glucosides such as methyl β-D-glucoside and p-nitrophenyl glucoside, as well as glycosides containing only carbohydrate residues, such as cellobiose. The catalysis of cellobiose by β-glucosidase is important because it produces glucose for the microorganism and further because the accumulation of cellobiose inhibits cellobiohydrolases and endoglucanases thus reducing the rate of hydrolysis of cellulose to glucose.

Since β-glucosidases can catalyze the hydrolysis of a number of different substrates, the use of this enzyme in a variety of different applications is possible. For instance, some β-glucosidases can be used to liberate aroma in fruit by catalyzing various glucosides present therein. Similarly, some β-glucosidases can hydrolyze grape monoterpenyl β-glucosidase which upon hydrolysis, represents an important potential source of aroma to wine as described by Gunata et al, "Hydrolysis of Grape Monoterpenyl β-D-Glucosides by Various β-Glucosidases", *J. Agric. Food Chem.*, Vol. 38, pp. 1232–1236 (1990).

Furthermore, cellulases can be used in conjunction with yeasts to degrade biomass to ethanol wherein the cellulose degrades cellobiose to glucose that yeasts can further ferment into ethanol. This production of ethanol from readily available sources of cellulose can provide a stable, renewable fuel source. The use of ethanol as a fuel has many advantages compared to petroleum fuel products such as a reduction in urban air pollution, smog, and ozone levels, thus enhancing the environment. Moreover, ethanol as a fuel source would reduce the reliance on foreign oil imports and petrochemical supplies.

But the major rate limiting step to ethanol production from biomass is the insufficient amount of β-glucosidase in the system to efficiently convert cellobiose to glucose. Therefore, a cellulase composition that contains an enhanced amount of β-glucosidase would be useful in ethanol production. contrarily, in some cases, it is desirable to produce a cellulase composition which is deficient in, and preferably free of β-glucosidase. Such compositions would be advantageous in the production of cellobiose and other cellooligosaccharides.

β-glucosidases are present in a variety of prokaryotic organisms, as well as eukaryotic organisms. The gene encoding β-glucosidase has been cloned from several prokaryotic organisms and the gene is able to direct the synthesis of detectable amounts of protein in *E. coli* without requiring extensive genetic engineering, although, in some cases, coupling with a promotor provided by the vector is required. However, β-glucosidases are not produced by such organisms in commercially feasible amounts.

Furthermore, such prokaryotic genes often cannot be expressed and detected after transformation of the eukaryotic host. Thus, in order to use fungal strains, fungal genes would have to be cloned using methods described herein or by detection with the *T. reesei* bg11 gene by nucleic acid hybridization.

The contribution and biochemistry of the β-glucosidase component in cellulose hydrolysis is complicated by the apparent multiplicity of enzyme forms associated with *T.* reesei and other fungal sources (Enari et al, "Purification of Trichoderma reesei and Aspergillus niger β-glucosidase", J. Appl. Biochem., Vol. 3, pp. 157–163 (1981); Umile et al, "A constitutive, plasma membrane bound β-glucosidase in Trichoderma reesei", FEMS Microbiology Letters, Vol. 34, pp. 291–295 (1986); Jackson et al, "Purification and partial characterization of an extracellular β-glucosidase of Trichoderma reesei using cathodic run, polyacrylamide gel electrophoresis", Biotechnol. Bioeng., Vol. 32, pp. 903–909 (1988)). These and many other authors report β-glucosidase enzymes ranging in size from 70–80 Kd and in pI from 7.5–8.5. More recent data suggests that the extracellular and cell wall associated forms of β-glucosidase are the same enzyme (Hofer et al, "A monoclonal antibody against the alkaline extracellular β-glucosidase from Trichoderma reesei: reactivity with other Trichoderma β-glucosidases", Biochim. Biophys. Acta, Vol. 992, pp. 298–306 (1989); Messner and Kubicek, "Evidence for a single, specific β-glucosidase in cell walls from Trichoderma reesei QM9414", Enzyme Microb. Technol., Vol. 12, pp. 685–690 (1990)) and that the variation in size and pI is a result of post translational modification and heterogeneous methods of enzyme purification. It is unknown whether the intracellular β-glucosidase species with a pI of 4.4 and an apparent molecular weight of 98,000 is a novel β-glucosidase (Inglin et al, "Partial purification and characterization of a new intracellular β-glucosidase of Trichoderma reesei", Biochem. J., Vol. 185, pp. 515–519 (1980)) or a proteolytic fragment of the alkaline extracellular β-glucosidase associated with another protein (Hofer et al, supra).

Since a major part of the detectable β-glucosidase activity remains bound to the cell wall (Kubicek, "Release of carboxymethylcellulase and β-glucosidase from cell walls of Trichoderma reesei", Eur. J. Appl. Biotechnol., Vol. 13, pp. 226–231 (1981); Messner and Kubicek, supra; Messner et al, "Isolation of a β-glucosidase binding and activating polysaccharide from cell walls of Trichoderma reesei", Arch. Microbiol., Vol. 154, pp. 150–155 (1990)), commercial preparations of cellulase are thought to be reduced in their ability to produce glucose because of relatively low concentrations of β-glucosidase in the purified cellulase preparation.

To overcome the problem of β-glucosidase being rate limiting in the production of glucose from cellulose using cellulase produced by a filamentous fungi, the art discloses supplementation of the cellulolytic system of Trichoderma reesei with the β-glucosidase of Aspergillus and the results indicate an increase in rate of saccharification of cellulose to glucose. Duff, Biotechnol Letters, 7, 185 (1985). Culturing conditions of the fungi have also been altered to increase β-glucosidase activity in Trichoderma reesei as illustrated in Sternberg et al, Can. J. Microbiol., 23, 139 (1977) and Tangnu et al, Biotechnol. Bioeng., 23, 1837 (1981), and mutant strains obtained by ultraviolet mutation have been reported to enhance the production of β-glucosidase in Trichoderma reesei. Although these aforementioned methods increase the amount of β-glucosidase in Trichoderma reesei, the methods lack practicality and, in many instances, are not commercially feasible.

A genetically engineered strain of Trichoderma reesei or other filamentous fungi that produces an increased amount of β-glucosidase would be ideal, not only to produce an efficient cellulase system, but to further use the increased levels of expression of the ball gene to produce a cellulase product that has increased cellulolytic capacity. Such a strain can be feasibly produced using transformation.

But, in order to transform mutant strains of Trichoderma reesei or other filamentous fungi, the amino acid sequence of the ball gene of Trichoderma reesei or the other filamentous fungi must be first characterized so that the bg11 gene can be cloned and introduced into mutant strains of Trichoderma reesei or other filamentous fungi.

Additionally, once the bg11 gene has been identified, information within linear fragments of the ball gene can be used to prepare strains of Trichoderma reesei and other filamentous fungi which produce cellulase compositions free of β-glucosidase.

Accordingly, this invention is directed, in part, to the characterization of the bg11 gene that encodes for extracellular or cell wall bound β-glucosidase from Trichoderma reesei and other filamentous fungi. This invention is further directed to the cloning of the bg11 gene into a plasmid vector that can be used in the transformation process, and to introduce the ball gene into the Trichoderma reesei or other filamentous fungi genome in multiple copies, thereby generating transformed strains which produce a cellulase composition having a significant increase in β-glucosidase activity. Moreover, cellulase compositions that contain increased cellulolytic capacity are also disclosed.

This invention is further directed, in part, to the deletion or disruption of the ball gene from the Trichoderma reesei or other filamentous fungi genome. In addition, altered copies of the bg11 gene which may change the properties of the enzyme can be reintroduced back into the Trichoderma reesei or other filamentous fungi genome.

SUMMARY OF THE INVENTION

The amino acid sequence of the extracellular or cell wall bound β-glucosidase protein from Trichoderma reesei has now been obtained in sufficient detail to enable the bg11 gene to be cloned into a suitable plasmid vector. The plasmid vector can then be used to transform strains of filamentous fungi to produce transformants which have multiple copies of the bg11 gene introduced therein.

Accordingly, in one of its process aspects, the present invention relates to a process for expressing enhanced extracellular β-glucosidase in a filamentous fungus comprising expressing a fungal DNA sequence encoding enhanced β-glucosidase in a recombinant host microorganism, said recombinant host microorganism being a filamentous fungus transformed with an expression vector containing said DNA sequence.

In another process aspect, the present invention relates to a process for expressing cellulases from a β-glucosidic filamentous fungi which are free of extracellular β-glucosidase.

In yet another process aspect, the present invention relates to a process for expressing an altered extracellular β-glucosidase in a filamentous fungus.

In another aspect, the present invention is directed to the amino acid sequence of extracellular β-glucosidase from Trichoderma reesei.

In yet another aspect, the present invention is directed to use of a nucleic acid fragment comprising the entire or partial nucleotide sequence of the T. reesei extracellular β-glucosidase gene as a probe to identify and clone out the equivalent bg11 gene from other β-glucosidic filamentous fungi.

In one of its composition aspects, the present invention is directed to novel and useful transformants of Trichoderma reesei, which can be used to produce fungal cellulase compositions, especially fungal cellulase compositions enriched in β-glucosidase or deleted of β-glucosidase. Also contemplated in the present invention is the alteration of the bg11 gene and the introduction of the altered bg11 gene into *T. reesei* to produce transformants which can also be used to produce altered fungal cellulase compositions.

In another composition aspect, the present invention is directed to fungal cellulase compositions prepared via the transformed *Trichoderma reesei* strains.

BRIEF DESCRIPTION OF THE DRAWINGS

FIG. 1 is the nucleotide sequence and deduced primary amino acid structure of the entire *T. reesei* bg11 gene.

FIG. 2 is a schematic representation of the vector pSASβ-glu.

FIG. 3A is a figurative representation of the vector pSASΔβGlu bal pyr (Δ36).

FIG. 3B is a figurative representation of the vector DUCΔβ-Glu A/R pyr (Δ12).

FIG. 4 represents a Northern blot of total RNA isolated from the transformed strains of *Trichoderma reesei* following induction with sophorose using the probes of cbh2 and a 700 bp fragment of bg11 cDNA.

FIG. 5A represents an autoradiograph of a Southern blot of *T. reesei* DNA illustrating the presence of β-glucosidase gene in wild type *T. reesei* (RL-P37) compared to strains of *T. reesei* genetically modified so as to not include the β-glucosidase gene (Δ12 and Δ36).

FIG. 5B represents an autoradiograph of a Northern blot of *T. reesei* RNA illustrating the expression of β-glucosidase gene in wild type *T. reesei* (RL-P37) compared to strains of *T. reesei* genetically modified so as to not include the β-glucosidase gene (Δ12 and Δ36).

FIG. 5C represents an analysis of the proteins expressed by P37 (wild type), Δ12, and Δ36 strains of *Trichorderma reesei* and illustrates the absence of β-glucosidase in the proteins expressed by Δ12 and Δ36 strains *Trichoderma reesei*.

FIG. 6 represents an autoradiograph of Hind III digested genomic DNA from a *T. reesei* overproducing strain and transformants of pSASβ-Glu, blotted and probed with the 700 bp β-Glu probe.

FIG. 7 represents a curve illustrating Avicel hydrolysis using the dosage, substrate:enzyme of 80:1 from an enriched recombinant β-glucosidase composition produced by the present invention.

FIG. 8 represents a curve illustrating PSC hydrolysis using the dosage, substrate:enzyme of 300:1 from an enriched recombinant β-glucosidase composition produced by the present invention.

FIG. 9 represents a curve illustrating the rate of hydrolysis of a cellulosic diaper derived fibers using an enriched recombinant β-glucosidase composition produced by the present invention.

FIGS. 10A and 10B are autoradiographs of *Aspergillus nidulans, Neurospora crassa, Humicola grisea* genomic DNA digested with Hind III and Eco RI, blotted and probed with a DNA fragment containing the bg11 gene of *Trichoderma reesei*.

DETAILED DESCRIPTION OF THE PREFERRED EMBODIMENTS OF THE INVENTION

As used herein, the term "enhanced extracellular β-glucosidase" or "enhanced β-glucosidase" means that at least one additional copy of a gene encoding for extracellular β-glucosidase has been introduced into the genome.

The term "devoid of the bg11 gene" means either that the bg11 gene has been deleted from the genome and therefore cannot be expressed by the recombinant host microorganism; or that the bg11 gene has been disrupted in the genome so that a functional extracellular β-glucosidase enzyme cannot be produced by the recombinant host microorganism.

The term "altered β-glucosidase" or "altered β-glucosidase gene" means that the amino acid sequence of the expressed protein has been altered by removing, adding, and/or manipulating the nucleic acid sequence of the gene or the amino acid sequence of the protein.

The term "by recombinant means" denotes that a microorganism has been transformed with a DNA molecule created in a test-tube by ligating together pieces of DNA that are not normally contiguous.

The term "cellulase free of extracellular β-glucosidase" refers to a cellulase composition which does not contain functional extracellular β-glucosidase enzyme. Such compositions are preferably prepared by culturing a filamentous fungi wherein the β-glucosidase gene has been either deleted or disrupted. Preferably, these compositions are prepared by culturing a filamentous fungi wherein the β-glucosidase gene has been deleted.

The term "filamentous fungi" means any and all art recognized filamentous fungi.

The term "β-glucosidic filamentous fungi" refers to those filamentous fungi which produce a cellulase composition containing β-glucosidase.

The term "cellooligosaccharide" refers to those oligosaccharide groups containing from 2–8 glucose units having β-1,4 linkages. Such cellooligosaccharides include cellobiose (diglucose having a β-1,4- linkage) and are preferably derived from cellulose.

More specifically, the present invention relates to the isolation and characterization of the bg11 gene coding for the extracellular or cell wall bound protein from *Trichoderma reesei* (sometimes referred to as "T. reesei") and the specific nucleotide and amino acid sequence of this gene. The bg11 gene is cloned into plasmid vectors, which are further used to produce transformed strains of *T. reesei* and other filamentous fungi having extra copies of the bg11 gene inserted therein. These transformants are then used to produce cellulase compositions having increased β-glucosidase activity and thus enhanced cellulolytic degradation.

Besides enhancing cellulolytic degradation by inserting extra copies of the bg11 gene into *T. reesei* strains, it is also contemplated by the present invention to produce transformed strains that are completely devoid of the bg11 gene.

Also contemplated by the present invention is the manipulation of the amino acid sequence in the bg11 gene itself. Alteration of the active sites on this enzyme may lead to a variety of different changes in catalytic conversion. For example, since β-glucosidase has both hydrolase and transferase activity, alteration of the amino acid sequence may result in the removal of hydrolase activity and an increase in transferase activity and, thus, facilitate the synthesis of B 1–4 oligo-dextrins. Moreover, manipulation of the amino acid sequence of β-glucosidase may result in further changes in the system, such as different pH optima, different temperature optima, altered catalytic turn over rate (Vmax), altered affinity (Km) for cellobiose leading to an increased affinity for cellobiose or a decreased affinity for cellobiose resulting in a slower or zero rate of reaction, altered product inhibition profile such that lower or higher levels of glucose will inhibit β-glucosidase activity, and the like.

Moreover, a nucleic acid fragment containing the entire nucleotide sequence of the extracellular β-glucosidase gene in *T. reesei* or a portion thereof can also be labeled and used as a probe to identify and clone out the equivalent bgl1 gene in other filamentous fungi.

Generally, the present invention involves the isolation of the bgl1 gene from *T. reesei* by identifying a 700 bp cDNA fragment of the gene which is then used as a probe to identify a single *T. reesei* fragment containing the bgl1 gene which was subsequently cloned. Because of the species homology of the bgl1 gene, a probe employing a fragment of the bgl1 gene of *T. reesei* can be employed to identify the bgl1 gene in other cellulolytic microorganisms and, it is understood that the following description for *T. reesei* could also be applied to other β-glusosidic filamentous fungi.

In the case of *T. reesei, this* 6.0 kb fragment is then cloned into a pUC plasmid and a series of mapping experiments are performed to confirm that the entire bgl1 gene is contained in this fragment. The nucleotide sequence is then determined on both strands and the position of two introns can be confirmed by sequence analysis of bgl1 cDNA subclones spanning the intron/exon boundaries. After isolation of the bgl1 gene, additional bgl1 gene copies are then introduced into *T. reesei* or other filamentous fungal strains to increase the expression of β-glucosidase.

In contrast, the entire bgl1 gene can also be deleted from the genome of *T. reesei* and other β-glucosidic filamentous fungi, thereby producing transformants that express cellulases free of β-glucosidase.

The isolation of the bgl1 gene from *T. reesei* involves the purification of extracellular β-glucosidase, chemical and proteolytic degradation of this protein, isolation and determination of the sequence of the proteolytic fragments and design of synthetic oligomer DNA probes using the protein sequence. The oligomeric probes are then further used to identify a 700 bp β-glucosidase cDNA fragment which can be labeled and employed to later identify a fragment that contains the entire bgl1 gene within the fragment from digested genomic DNA from *T. reesei*.

To identify a feasible cDNA fragment that can be used as a probe for future analysis, total RNA is first isolated from *T. reesei* mycelia and polyadenylated RNA isolated therefrom. The polyadenylated RNA is then used to produce a cDNA pool which is then amplified using specific oligonucleotide primers that amplify only the specific cDNA fragment encoding the *T. reesei* bgl1 gene.

More specifically, total RNA is first isolated from a starting strain of *T. reesei*. The starting strain employed in the present invention can be any *T. reesei* cellulase overproduction strain that is known in the art. This cellulase producing strain is generally developed by ordinary mutagenesis and selection methods known in the art from any *T. reesei* strain. Confirmation that the selected strain overproduces cellulases can be performed by using known analysis methods. A preferred strain is RLP37 which is readily accessible.

A mycelial inoculum from the *T. reesei* over production strain, grown in an appropriate growth medium, is added to a basal medium and incubated for a period of between 50–65 hours at a temperature between 25° C. to 32° C., preferably 30° C. Fresh basal medium can be replaced during this incubation period. The culture medium is then centrifuged, and the mycelia is isolated therefrom and washed. The mycelia is then resuspended in a buffer to permit growth thereof and 1 mM sophorose (a β,1–2 dimer of glucose) is added to the mycelia to induce the production of cellulase enzymes. The mycelia preparation is then incubated for an additional time period, preferably 18 hours at 30° C. prior to harvesting.

Total RNA can be isolated from the mycelia preparation by a variety of methods known in the art, such as proteinase K lysis, followed by phenol:chloroform extraction, guanidinium isothiocyanate extraction, followed by cesium chloride gradients, guanidine hydrochloride and organic solvent extraction, and the like. It is preferable to isolate total RNA via the procedure described by Timberlake et al in "Organization of a Gene Cluster Expressed Specifically in the Asexual Spores of *A. nidulans,*" *Cell,* 26, pp. 29–37 (1981). The mycelia is isolated from the culture medium via filtration. Then the RNA is extracted from the mycelia by the addition of an extraction buffer, TE-saturated phenol and chloroform. The aqueous phase is removed and the organic phase is reextracted with the extraction buffer alone by heating the extraction mixture in a water bath at a temperature between about 60° C. to 80° C., preferably 68° C. to release the RNA trapped in polysomes and at the interface. All of the extracted aqueous phases are then pooled, centrifuged and reextracted with phenol-chloroform until there is no longer any protein at the interface. The RNA is further precipitated with 0.1 volume of 3 M sodium acetate and 2 volumes of 95% ethanol and pelleted via centrifugation before it is resuspended in DEP-water containing an RNase inhibitor.

The total RNA is then fractionated on 1% formaldehyde-agarose gels, blotted to Nytran™ membranes, and probed using a fragment of the *T. reesei* cbh2 gene to determine whether the genes encoding the enzymes of the cellulase system in the *T. reesei* preparation are indeed induced by addition of the sophorose. Basically, the probe used in the present invention is derived from a CBH II clone produced by methods known in the art. For more specific detail of how the clone was produced see Chen et al, "Nucleotide Sequence and Deduced Primary Structure of Cellobiohydrolase II from *Trichoderma reesei,*" *Bio/Technology,* Vol. 5 (March 1987). Site directed mutagenesis was performed on the CBH II clone and a bgl II site was placed at the exact 5' end of the open reading frame and a Nhe I site at the exact 3' end. The Bgl II and Nhe I restriction fragment containing CBH II coding sequence was further cloned into a pUC218 phagemid. The CBH II gene was further cut and gel isolated prior to adding a label.

The results of the Northern blot of *T. reesei* RNA probed with the cbh2 probe indicated that the level of cbh2 specific mRNA reached a peak at 14–18 hours post induction. From this data it can be inferred that the entire cellulase complex including β-glucosidase is induced at this time. The total RNA from 14, 18 and 22 hours is then pooled.

After pooling the specific fractions of total RNA, polyadenylated mRNA is further isolated from the total RNA. Postranscriptional polyadenylation is a common feature of the biogenesis of most eukaryotic mRNAs. The newly synthesized mRNAs have long poly(A) tracts which tend to shorten as mRNAs age. The newly synthesized polyadenylated mRNA is further isolated from total RNA by methods known in the art. These methods include the use of oligo (dT)-cellulose, poly(U) Sepharose, adsorption to and elution from poly(U) filters or nitrocellulose membrane filters, and the like. It is preferable to use oligo(dT) cellulose chromatography in isolating MRNA following the procedure described by Sambrook et al, *Molecular Cloning, A Laboratory Manual,* 2nd Edition, Cold Spring Harbor Laboratory Press (1989). More specifically, fractions of total RNA are run through the chromatographic resin, and mRNA is eluted therefrom with an elution buffer. The RNA which binds to the column is enriched for RNAs containing poly(A) tails and, therefore, eliminates contaminants, such as rRNA and partially degraded mRNAs. It is important that the purification be carried out successfully such that when cDNA is synthesized from the mRNA, higher yields of mRNA copies and less spurious copying of non-messenger RNAs occurs.

Total RNA and polyadenylated RNA from the preparations were further fractionated on 1% formaldehyde gels, blotted to Nytran[R] membranes and analyzed to confirm that the enzymes in the cellulase complex were being induced as polyadenylated mRNA.

After isolating polyadenylated mRNA from total RNA, complementary DNA or cDNA is synthesized therefrom. The first strand of cDNA is synthesized using the enzyme RNA-dependent DNA polymerase (reverse transcriptase) to catalyze the reaction. Avian reverse transcriptase which is purified from the particles of an avian retrovirus or murine reverse transcriptase, which is isolated from a strain of $E.$ $coli$ that expresses a cloned copy of the reverse transcriptase gene of the Moloney murine leukemia virus can be used in the present invention. However, it is preferable to use the Moloney murine leukemia virus (M-MLV) reverse transcriptase to synthesize first strand cDNA from the polyadenylated mRNA population. The amount of cloned M-MLV reverse transcriptase required may vary depending on the amount of polyadenylated mRNA used in the synthesis reaction. Usually, about 200 U/μl of the reverse transcriptase is used per 2 to 10 μg of mRNA per reaction.

Also present in the synthesis mixture is a primer to initiate synthesis of DNA. For cloning of cDNAs, any primer can be used, but it is preferable to use oligo(dT) containing 12–18 nucleotides in length, which binds to the poly(A) tract at the 3' terminus of eukaryotic cellular mRNA molecules. The primer is added to the reaction mixture in large molar excess so that each molecule of mRNA binds several molecules of oligo(dT)$_{12-18}$. It is preferable to use about 12.5 μg of primer having a concentration of 0.5 mg/ml.

Besides the enzyme and primer, a buffer and dNTP mix containing DATP, dCTP, dGTP, and dTTP at a final concentration of 500 μM each usually completes the reaction cocktail. Any buffer can be used in the present invention for first strand cDNA synthesis that is compatible with this synthesis. It is preferable to use a buffering system consisting of 250 mM Tris-HCl (pH 8.3), 375 mM KCl, 15 mM MgCl$_2$, and 50 mM dithiothreitol. Generally, about 500 μl of buffer completes the synthesis solution.

After the first strand is synthesized, the second strand of cDNA may be synthesized by a variety of methods known in the art, such as hairpin-primed synthesis by denaturing the cDNA:mRNA complex, adding the Klenow fragment of $E.coli$ DNA polymerase or reverse transcriptase, and then digesting the hairpin loop with nuclease S1 to obtain a double-stranded cDNA molecule, the Okayama and Berg method, the Gubler and Hoffman method, and the like. The Okayama and Berg method uses $E.$ $coli$ RNase H to randomly nick the mRNA, and the RNA is replaced in the nick translation reaction by catalysis with $E.$ $coli$ DNA polymerase I. In the Okayama and Berg method, mRNA is used to prime DNA synthesis by the $E.$ $coli$ DNA polymerase I.

The preferred method to synthesize the second strand of cDNA is a modified method of the Gubler and Hoffman procedure. This procedure uses $E.$ $coli$ RNase H, DNA Polymerase I, and DNA Ligase to form the second strand. Actually, two different methods of proceeding with the second strand synthesis can be used in the present invention. The first procedure uses RNase H to attack the RNA:DNA hybrid in a random fashion, producing nicks in addition to those produced by reverse transcriptase. If too many nicks are introduced into the RNA at the 51 end of the message before second strand synthesis commences, fragments may be produced that are too short to remain hybridized; thus, they will not be able to serve as primers. In addition, the 5'-most RNA oligomer which primes second strand DNA synthesis will continue to be degraded until only two ribonucleotides remain at the 5' end of the second strand DNA. These are substrates for the polymerase I RNase H activity, and the remaining nucleotides will be removed. This leaves the 3' end of the first strand cDNA single stranded, making it a substrate for the 3' exonuclease activity of Polymerase I. The result is a population of cDNAs, which are blunt-ended.

An alternative method relies on M-MLV reverse transcriptase to produce nicks 10 to 20 bases from the 5' end of the RNA in the hybrid. DNA polymerase I is then used for synthesis. Generally, about 500 units at a concentration of 10 U/μl of DNA polymerase I is used. After second strand synthesis, RNase H is added after removal of the DNA polymerase I to produce a duplex, which is entirely DNA, except for the surviving capped RNA 5' oligonucleotide.

The second-strand synthesis by either procedure set forth above usually takes place in the presence of a buffer and dNTP mix. Any buffering system that is known in the art for second strand cDNA synthesis can be used; however, it is preferable to use a buffering system containing 188 mM Tris-HCl, pH 8.3, 906 mM KCl, 100 mM (NH$_4$)$_2$SO$_4$, 46 mM MgCl$_2$, 37.5 mM dithiothreitol, and 1.5 mM HAD. The dNTP mix preferably contains 10 mM DATP, 10 mM dCTP, 10 mM dGTP, and 10 mM dTTP.

The second strand synthesis is carried out under known procedures set forth in the art. The preferred methods and reagents used to synthesize cDNA in the present invention are the BRL cDNA Synthesis System[R] (Bethesda Research Laboratories, Gaithersburg, Md.) and the Librarium System (Invitrogen, San Diego, Calif.).

At this point a pool of cDNAs, a small portion of which code for the bg11 gene, is present after second strand synthesis. Since amplification of only the specific bg11 gene fragment in the cDNA pool is crucial for the isolation of the β-glucosidase gene, specific primers were designed to amplify the cDNA fragment encoding the $T.$ $reesei$ bg11 gene in the polymerase chain reaction (PCR). The primers used are degenerate primers designed to hybridize to the cDNA of the bg11 gene encoding the N-terminus and an internal CNBr fragment.

In general, it is difficult to isolate the bg11 gene because the amino acid sequence of the protein does not contain sufficient amino acids which are coded for by unique nucleic acid triplets and thus any oligonucleotide used would be too degenerate to specifically amplify the bg11 gene in the PCR reaction. However, in this invention, primers were designed by examining the amino acids of the region targeted for amplification of mature β-glucosidase and choosing regions, which will require a reduced degree of degeneracy in the genetic code. Codon bias in $T.$ $reesei$ for various other cellulase genes such as cbh1, cbh2, eg11, and the like was also taken into account when designing the oligonucleotide primers. More specifically, codon bias is based on various genes in the strain $T.$ $reesei$ which display a preferred nucleotide triplet encoding different amino acids. By analyzing this codon bias one can determine that a particular nucleotide sequence coding for an amino acid would be preferred. For example, the cbh1, cbh2 and eg1 genes from $T.$ $reesei$ prefer the CCU coding for the amino acid proline. Thus, when designing an oligonucleotide probe, the CUG sequence would be the preferred choice for leucine, rather than the other triplets (CUU, CUC, CUA, UUA and CUG) which code for leucine.

Furthermore, after selection of an N-terminal region and an internal region as primers for amplification purposes, the primers were designed by inserting a non-specific base inosine into the wobble position of the primer for the N-terminus and using a pool of sixteen variable primer sequences for the internal primer. Basically, the creation of degenerate primers is described by Compton in "Degenerate Primers For DNA Amplification" and Lee et al in "cDNA Cloning Using Degenerate Primers" in *PCR Protocols: A Guide to Methods and Applications,* published by Academic Press (1990).

Using the primers described above, the cDNA sequences encoding the amino terminal region of the bg11 gene is then selectively amplified using PCR. The amplification method consists of an initial, denaturing cycle of between about 5 to 15 minutes at 95° C., followed by a 1–7 minutes annealing step at a temperature between 35° C. and 55° C. and preferably between 45° C. and 55° C. and a 5–15 minutes polymerization cycle at 65° C. It is preferable, however, to use a 10 minute initial denaturing cycle, followed by 2 minutes of annealing at 50° C. and a 10 minute, and preferably a 30 minute polymerization cycle at the aforedescribed temperatures.

The amplified fragment is then identified via gel electrophoresis as a 700 bp cDNA segment. The amplified pool of cDNAs is then further fractionated on a polyacrylamide gel to obtain a more purified 700 bp cDNA fragment for cloning purposes. After elution of the 700 bp fragments from the gel, the 700 bp cDNA fragments are then cloned into phagemid vectors. Any cloning vector can be used to clone the cDNA bg11 gene fragments, such as pUC18, pUC19, pUC118, pUC119, pBR322, pEMBL, pRSA101, pBluescript, and the like. However, it is preferable to use the cloning vectors pUC218 and pUC219, which are derived from pUC18 and pUC19 by insertion of the intergenic region of M13. The cloning vectors with the cDNA fragments containing the bg11 gene are then used to transform *E. coli* strain JM101. After transformation, positive colonies containing the bg11 gene were identified and DNA isolated therefrom using chloroform:phenol extraction and ethanol precipitation methods.

The nucleotide sequence of the subcloned cDNA 700 bp fragment is then determined by the dideoxy chain termination method described by Sanger et al using a Sequenase$^R$ reagent kit provided by U.S. Biochemicals.

From this nucleotide sequence it was determined that the subcloned 700 bp cDNA segment contained an open reading frame encoding 150 amino acids that overlapped a number of other sequenced peptides that were obtained following CNBr and proteolytic degradation of purified *T. reesei* β-glucosidase. Thus, it was confirmed that the cloned sequences encoded for the extracellular *T. reesei* β-glucosidase protein.

The cloning of the genomic version of the entire β-glucosidase gene was then undertaken by labelling the 700 bp bg11 cDNA fragment with $^{32}$p using the methods to label oligonucleotides described by Sambrook et al, supra. This probe is used to identify a 6.0 kb band on a Southern blot of Hind III digested genomic DNA from *T. reesei.*

The genomic DNA from *T. reesei* is prepared for Southern blot analysis by deproteinizing the genomic DNA, followed by treatment with ribonuclease A. The prepared genomic DNA is then cut with one of a variety of restriction enzymes such as Eco RI, Hind III and the like, run on a gel, Southern blotted and hybridized with the 700 bp cDNA labelled fragment of the bg11 gene. From this analysis, it was determined that Hind III was the restriction enzyme of choice that can be used to clone the bg11 gene.

Hind III is then added to genomic DNA from the strain *T. reesei* and DNA is extracted therefrom. A sample from this digestion is run on an agarose gel and fractionated electrophoretically. The gel is then Southern blotted and probed with the 700 bp cDNA probe. A 6.0 kb band was then identified on the Southern blot of Hind III digested genomic DNA. The remaining Hind III digested genomic DNA was then subjected to preparative gel electrophoresis and DNA ranging in size from about 5.0 kb to 7.0 kb was eluted therefrom and cloned into a phagemid vector and used to transform *E. coli* JM101 to create a library. Any phagemid vector can be used such as those described above, however it is preferable to use pUC218. The colonies that resulted from the transformation were then subjected to colony hybridization using the 700 bp cDNA fragment as a probe to identify those colonies that contained the cloned genomic DNA coding for bg11 . The positive colonies from the transformation are then picked and the DNA isolated therefrom by methods known in the art.

The isolated DNA from such a positive colony is then digested with various restriction enzymes, both singly and in various combinations, and subjected to agarose gel electrophoresis. The resultant banding pattern is then used to construct a restriction map of the cloned 6.0 kb genomic DNA from *T. reesei.* Enzymes used in the digestion include Eco RI, Sst I, Kpn I, Sma I, Bam HI, Xho 1, Bgl II, Cla I, Xba I, Sal I, Pst I, Sph I, Hind III, Bal I, Pvu II and the like.

The same gel is then subject to Southern blot analysis using the same 700 bp bg11 cDNA as a probe to identify which genomic restriction fragments shared homology with the bg11 cDNA. Since the position of these homologous fragments can be determined relative to the restriction map of the 6.0 kb genomic fragment and also since the size of the β-glucosidase protein (74 kd) gives an estimated length of the gene as 2.1 kb (because average molecular weight of an amino acid is 105 daltons, a 74 kd protein contains on average 705 amino acids, which in turn is equal to 2,115 bp), then the mapping experiments confirmed that the entire bg11 gene is contained on the genomic Hind III clone.

Pvu II and Bal I restriction fragments ranging in size from 600 bp to 1500 bp hybridized with the 700 bp cDNA bg11 clone and were thus chosen for subcloning into pUC218 phagemids. The nucleotide sequence was determined using the methods of Sanger et al, described above. The Pvu II and Bal I subclones were sequenced and the overlapping sequences of the subclones aligned until a single contiguous sequence totaling 3033 bp was obtained within which the nucleotide sequence of the bg11 gene was determined on both strands and the position of two small introns was inferred by homology to introns of other genes of filamentous fungi. The amino acid sequence is also deduced as set forth in FIG. 1.

The nucleotide sequence and deduced primary amino acid sequence of the entire *T. reesei* bg11 gene is set forth in FIG. 1 (SEQ ID NO:1). The predicted molecular weight of the encoded β-glucosidase protein is 74,341. A 31 amino acid peptide precedes the mature amino terminus of β-glucosidase as deduced from the amino terminal peptide sequence. Within this peptide, there are three potential signal peptidase recognition sites consisting of Ala-X-Ala.

The primary amino acid sequence of β-glucosidase (SEQ ID NO:2) shows 7 potential N-linked glycosylation sites at positions 208, 310, 417, and 566, which shows the consensus Asn-X-Ser/Thr-X where X is not a proline. However, sites at positions 45, 566, and 658 have a proline residue in the consensus sequence and may or may not be glycosylated.

No unusual codon bias is observed in the bg11 gene when compared to other cellulase genes. The bg11 coding region is interrupted by two short introns of 70 bp and 64 bp, respectively. Both introns have splice site donor, splice acceptor, and lariat branch acceptor sites that show homology to the consensus splice signals emerging from *T. reesei* and other filamentous fungi.

Since the bg11 gene from the *T. reesei* strain is identified and can be cloned, the next step is to produce a transformant that has extra copies of the bg11 gene.

A selectable marker must first be chosen so as to enable detection of the transformed filamentous fungus. Different selectable markers may be used including argB from *A. nidulans* or *T. reesei*, amdS from *A. nidulans*, pyr4 from *Neurospora crassa*, *A. nidulans* or *T. reesei*, and pyrG from *Aspergillus niger*. The selectable marker can be derived from a gene, which specifies a novel phenotype, such as the ability to utilize a metabolite that is usually not metabolized by the filamentous fungi to be transformed or the ability to resist toxic shock effects of a chemical or an antibiotic. Also contemplated within the present invention are synthetic gene markers that can be synthesized by methods known in the art. Transformants can then be selected on the basis of the selectable marker introduced therein. Because *T. reesei* does not contain the amdS gene, it is preferable to use the amdS gene in *T. reesei* as a selectable marker that encodes the enzyme acetamidase, which allows transformant cells to grow on acetamide as a nitrogen source. In the case where the bg11 gene is deleted from *T. reesei*, it is preferable to use the pyrG gene as a selectable marker.

The host strain used should be mutants of the filamentous fungi which lack or have a nonfunctional gene or genes corresponding to the selectable marker chosen. For example, if the selectable marker of argB is used, then a specific arg mutant strain is used as a recipient in the transformation procedure. Other examples of selectable markers that can be used in the present invention include the genes trp, pyr4, pyrG, trp1, oliC31, Bm1, pkiA, niaD, leu, and the like. The corresponding recipient strain must, therefore, be a mutant strain such as trp⁻¹ pyr⁻¹ leu⁻¹ and the like.

The mutant strain is derived from a starting host strain, which is any filamentous fungi strain. However, it is preferable to use a filamentous fungi over-producing mutant strain and particularly, a *T. reesei* overproducing strain described previously, since this strain secretes high amounts of proteins and, in particular, high amounts of cellulase enzymes. The selected mutant strain is then used in the transformation process. The preferred strain of *T. reesei* for use in deleting the bglI gene is RLP37 pyrG69, a uridine auxotroph.

The mutant strain of the selected filamentous fungi can be prepared by a number of techniques known in the art, such as the filtration enrichment technique described by Nevalainen in "Genetic improvement of enzyme production in industrially important fungal strains", Technical Research Center of Finland, Publications 26 (1985). Another technique to obtain the mutant strain is to identify the mutants under different growth medium conditions. For instance, the arg mutants can be identified by using a series of minimal plates supplied by different intermediates in arginine biosynthesis. Another example is the production of pyr⁻ mutant strains by subjecting the strains to fluoroorotic acid (FOA).

Strains with an intact pvr4 gene grow in an uridine medium and are sensitive to fluoroorotic acid, and, therefore, it is possible to select pyr4- mutant strains by selecting for FOA resistance.

The chosen selectable marker is then cloned into a suitable plasmid. Any plasmid can be used in the present invention for the cloning of the selectable marker such as pUC18, pBR322, and the like. However, it is preferable to use pUC100. The vector is created by digesting pUC100 with the restriction enzyme SmaI, and the 5' phosphate groups are then removed by digestion with calf alkaline phosphatase. The fragment vector is then purified by gel electrophoresis followed by electroelution from the isolated gel slice. The amds gene from *A. nidulans is isolated as a* 2.4 kb SstI restriction fragment following separation of the vector sequences via known procedures such as those described by Hynes et al, *Mol, Cell. Biol.*, 3, pp. 1430–1439 (1983). The 2.4 Kb SstI amdS fragment and the 2.7 Kb pUC100 vector fragment are then ligated together, and the ligation mix is then introduced into the *E. coli* host strain JM101.

Any plasmid can be used in the present invention for the insertion of the bg11 gene, but it is preferable to use the pSAS plasmid. pSASβ-glu is constructed by digesting pSAS with the restriction enzyme Hind III and purifying the linear fragment via gel electrophoreses and electroelution. Into this Hind III treated pSAS vector fragment is ligated the 6.0 Kb Hind III fragment of *T. reesei* genomic DNA that contained all of the coding region of the bg11 gene along with the sequences necessary for transcription and translation. FIG. 2 illustrates the construction of pSASβ-glu.

It is also possible to construct vectors that contain at least one additional copy of the bg11 gene and to construct vectors in which the amino acid sequence of bg11 gene has been altered by known techniques in the art such as site directed mutagenesis, PCR methods, and chemical mutation methods.

In another embodiment, the bg11 gene of a β-glucosidic filamentous fungi can be totally deleted and may be replaced with other known genes. Preferably, the replacing gene is homologous to the filamentous fungi so that the resulting recombinant microorganism does not express any heterologous protein. For example, potentially any *T. reesei* gene which clones for a selected marker and which has been cloned and thus identified in the genome, can replace the bg11 gene in *T. reesei* using the techniques described herein.

On the other hand, the replacing gene does not necessarily have to be homologous. Specifically, for the deletion of the bg11 gene in *T. reesei*, vectors containing heterologous gene which have been used are illustrated in FIGS. 3A and 3B. In FIG. 3B, a pUC218 vector plasmid having the *Aspergillus niger* pyrG gene inserted therein is illustrated. A 6.0 Kb genomic Hin dIII fragment, known to contain the entire bg11 gene, is cloned into the polylinker of pUC218. The coding region for the bg11 gene is then removed from this plasmid using either unique Ball restriction sites (FIG. 3A) or unique ApaI and EcoRV restriction sites (FIG. 3B) situated at the very 5' and 3' end of the bglI open reading frame and replaced with an isolated 2412 bp Hin dIII/Bam HI restriction fragment containing the pyrG gene from Asperaillus niger. All restriction ends are made blunt by treatment with T4 DNA polymerase prior to ligation using T4 DNA ligase.

After a suitable vector is constructed, it is used to transform strains of filamentous fungi. Since the permeability of the cell wall in filamentous fungi (e.g., *T. reesei*) is very low, uptake of the desired DNA sequence, gene or gene fragment is at best minimal. To overcome this problem, the permeability of the cell wall can be increased or the DNA can be directly shot into the cells via a particle gun approach. In the particle gun approach, the DNA to be incorporated into the cells is coated onto micron size beads and these beads are literally shot into the cells leaving the DNA therein and leaving a hole in the cell membrane. The cell then self-repairs the cell membrane leaving the DNA incorporated therein. Besides this aforedescribed method, there are a number of methods to increase the permeability of filamentous fungi cells walls in the mutant strain (i.e., lacking a functional gene corresponding to the used selectable marker) prior to the transformation process.

One method involves the addition of alkali or alkaline ions at high concentrations to filamentous fungi cells. Any alkali metal or alkaline earth metal ion can be used in the present invention; however, it is preferable to use either $CaCl_2$ or lithium acetate and more preferable to use lithium acetate. The concentration of the alkali or alkaline ions may vary depending on the ion used, and usually between 0.05 M to 0.4 M concentrations are used. It is preferable to use about a 0.1 M concentration.

Another method that can be used to induce cell wall permeability to enhance DNA uptake in filamentous fungi is to resuspend the cells in a growth medium supplemented with sorbitol and carrier calf thymus DNA. Glass beads are then added to the supplemented medium, and the mixture is vortexed at high speed for about 30 seconds. This treatment disrupts the cell walls, but may kill many of the cells.

Yet another method to prepare filamentous fungi for transformation involves the preparation of protoplasts. Fungal mycelium is a source of protoplasts, so that the mycelium can be isolated from the cells. The protoplast preparations are then protected by the presence of an osmotic stabilizer in the suspending medium. These stabilizers include sorbitol, mannitol, sodium chloride, magnesium sulfate, and the like. Usually, the concentration of these stabilizers varies between 0.8 M to 1.2 M. It is preferable to use about a 1.2 M solution of sorbitol in the suspension medium.

Uptake of the DNA into the host mutant filamentous fungi strain is dependent upon the concentration of calcium ion. Generally, between about 10 mM $CaCl_2$ and 50 mM $CaCl_2$ is used in an uptake solution. Besides the need for calcium ions in the uptake solution, other items generally included are a buffering system such as TE buffer (10 mM Tris, pH 7.4; 1 mM EDTA) or 10 mM MOPS, pH 6.0 buffer (morpholinepropane-sulfonic acid), and polyethylene glycol (PEG). The polyethylene glycol acts to fuse the cell membranes, thus permitting the contents of the mycelium to be delivered into the cytoplasm of the filamentous fungi mutant strain and the plasmid DNA is transferred to the nucleus. This fusion frequently leaves multiple copies of the plasmid DNA tandemly integrated into the host chromosome. Generally, a high concentration of PEG is used in the uptake solution. Up to 10 volumes of 25% PEG 4000 can be used in the uptake solution. However, it is preferable to add about 4 volumes in the uptake solution. Additives such as dimethyl sulfoxide, heparin spermidine, potassium chloride, and the like may also be added to the uptake solution and aid in transformation.

Usually a suspension containing the filamentous fungi mutant cells that have been subjected to a permeability treatment or protoplasts at a density of $10^8$ to $10^9$/ml, preferably $2 \times 10^8$/ml, are used in transformation. These protoplasts or cells are added to the uptake solution, along with the desired transformant vector containing a selectable marker and other genes of interest to form a transformation mixture.

The mixture is then incubated at 4° C. for a period between 10 to 30 minutes. Additional PEG is then added to the uptake solution to further enhance the uptake of the desired gene or DNA sequence. The PEG may be added in volumes of up to 10 times the volume of the transformation mixture, preferably, about 9 times. After the PEG is added, the transformation mixture is then incubated at room temperature before the addition of a sorbitol and $CaCl_2$ solution. The protoplast suspension is then further added to molten aliquots of a growth medium. This growth medium contains no uridine and selectively permits the growth of transformants only. The subsequent colonies were transferred and purified on a growth medium depleted of sorbitol.

At this stage, stable transformants can be distinguished from unstable transformants by their faster growth rate and the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

In order to ensure that the transformation took place by the above-described methods, further analysis is performed on the transformants such as Southern blotting and autoradiography. Using the same basic procedures set forth above, the entire bg11 gene can be deleted from a vector and transformed into filamentous fungi strains or the bg11 gene can be altered and transformed into filamentous fungi strains.

After confirmation that the transformed strains contained at least one additional copy of the bg11 gene, an altered bg11 gene or the transformants contained a deleted bg11 gene, the strains are further cultured under conditions permitting these transformants to propagate. The transformants can then be isolated from the culture media and used in a variety of applications which are described below. Alternatively, the transformants can be further fermented and a recombinant fungal cellulase composition can be isolated from the culture media. Since, for example, the transformants produced by the present invention can express enhanced, deleted or altered extracellular β-glucosidase in the fermentation medium, fungal cellulase compositions can be isolated from the medium. Usually, the isolation procedure involves centrifuging the culture or fermentation medium containing the transformants and filtering by ultrafiltration the supernatant to obtain a recombinantly produced fungal cellulase composition. Optionally, an antimicrobial agent can be further added to the composition prior to use in the variety of applications described below. Examples of microbial agents that can be added are sodium azide, sodium benzoate and the like.

Confirmation that the transformants produced by the process of the present invention had enhanced activity on cellobiose, the following experiment was performed. In this experiment 50 mg of cellobiose which was suspended in 1.0 ml of phosphate buffer (pH 5.0) and was reacted with the fermentation product produced by the transformant (65.5 mg/ml protein) using a fermentation product from a normal nonmutant *T. reesei* strain as a control (135.0 mg/ml protein). The results of cellobiase activity under conditions of initial rate, are set forth in Table I below:

TABLE I

| Product | Protein (mg/ml) | Activity on Cellobiose µmole glucose mg protein |
|---|---|---|
| Control | 135.0 | 6 |
| Product produced by the present invention | 65.5 | 33 |

The results from this experiment indicate that the fermentation product produced by the transformants of the present invention has over five times the specific activity on the substrate, cellobiose, compared to a nonmutant *T. reesei* control strain.

Moreover, FIGS. 7 and 8 confirm that hydrolysis is enhanced for the substrates Avicel and PSC (note: PSC is a phosphoric acid swollen cellulose obtained by treating Avicel with phosphoric acid) using 1.0% enzyme/substrate. In the experiment, PSC or Avicel was suspended in 2 mls of 50 mM sodium acetate buffer, pH 4.8, and incubated at 40° under non-agitated conditions for up to 24 hours. Soluble reducing sugar was measured by the method of Nelson and Somogyi. From these figures it is further demonstrated that the enhanced recombinant β-glucosidase fermentation product produced from transformants according to the present invention, has an increased rate and extent of hydrolytic activity on the various substrates compared to the standard Cyt-123 control (on average 20% higher activity). The Cyt-123 control is the product obtained from a *T. reesei* cellulase over-production strain subjected to fermentation on an industrial scale.

The enriched transformants can be used in a variety of different applications. For instance, some β-glucosidases can be further isolated from the culture medium containing the enhanced transformants and added to grapes during wine making to enhance the potential aroma of the finished wine product. Yet another application can be to use β-glucosidase in fruit to enhance the aroma thereof. Alternatively, the isolated recombinant fermentation product containing enhanced β-glucosidase can be used directly in food additives or wine processing to enhance the flavor and aroma.

Since the rate of hydrolysis of cellulosic products is increased by using the transformants having at least one additional copy of the bg11 gene inserted into the genome, products that contain cellulose or heteroglycans can be degraded at a faster rate and to a greater extent. Products made from cellulose such as paper, cotton, cellulosic diapers and the like can be degraded more efficiently in a landfill. FIG. 9 illustrates the use of an increased β-glucosidase preparation isolated from the fermentation medium containing transformants having at least one additional copy of the bg11 gene inserted into the genome compared to a non-enhanced Cyt 123 standard (defined above) on a cellulosic diaper product. This hydrolysis experiment was performed using 0.4 mg of the standard and the fermentation product per 100 mg of substrate (the cellulosic diaper). The experiment was run at 50° C. over a period of five hours and the glucose concentration was measured, in duplicate, at various time intervals. This curve illustrates an increased rate of hydrolysis for the product produced by the fermentation product derived from the transformant having additional copies of bg11, compared to the standard. It was also determined that the diaper derived fibers were about 14% insoluble in aqueous solution. Thus, the fermentation product obtained from the transformants or the transformants alone can be used in compositions to help degrade by liquefaction a variety of cellulose products that add to overcrowded landfills.

Simultaneous saccharification and fermentation is a process whereby cellulose present in biomass is converted to glucose and, at the same time and in the same reactor, yeast strains convert the glucose into ethanol. Yeast strains that are known for use in this type of process include *B. clausenii, S. cerevisiae, Cellulolyticus acidothermo- philium, C. brassicae, C. lustinaniae, S. uvarum, Schizosaccharomyces pombe* and the like. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, one major problem encountered in this process is the lack of β-glucosidase in the system to convert cellobiose to glucose. It is known that cellobiose acts as an inhibitor of cellobiohydrolases and endoglucanases and thereby reduces the rate of hydrolysis for the entire cellulase system. Therefore, the use of increased β-glucosidase activity to quickly convert cellobiose into glucose would greatly enhance the production of ethanol. To illustrate this point, cytolase 123 and the fermentation product produced by the transformants (normalized to cytolase on a total protein basis) according to the present invention under fermentation conditions were compared for their ability to hydrolyze crude paper fractions composed of 50–60% cellulosics from a fiber fraction (RDF) of municipal solid waste (MSW). Such suspensions were in 50 mM sodium acetate buffer, pH 4.8 to 5.0, and equilibrated at 30° C. The flasks were then dosed with 4% *Saccharomyces cerevisiae* and sampled periodically to 80 hours. The ethanol production yield was then measured. The following Table II illustrates that increased ethanol production is possible using the increased β-glucosidase preparation from the present invention using municipal solid waste preparations as the cellulosic source.

TABLE II

| Dosage | Grams/Liter Ethanol | |
|---|---|---|
| mg Protein gram cellulose | Cytolase 123 | High β-Glu Prep |
| 10 | 2.1 | 5.0 |
| 20 | 5.3 | 7.2 |
| 30 | 6.9 | 8.8 |
| 40 | 8.0 | 9.3 |
| 50 | 8.5 | 9.3 |
| 60 | 8.5 | 9.3 |

From Table II it can be clearly seen that the enhance β-glucosidase preparation prepared according to the present invention enhances the production of ethanol compared to a cytolase 123 control, especially at the lower protein concentrations.

In yet another embodiment of this invention, the deletion of the bg11 gene from *T. reesei* strains would be particularly useful in preparing cellulase compositions for use in detergents and in isolating cellooligosaccharides (e.g., cellobiose).

The cellulase enzymes have been used in a variety of detergent compositions to enzymatically soften clothes and to provide color restoration. However, it is known in this art that use of cellulase enzymes can impart degradation of the cellulose fibers in clothes. One possibility to decrease the degradation effect is to produce a detergent that does not contain β-glucosidase. Thus, the deletion of this protein would effect the cellulase system to inhibit the other components via accumulation of cellobiose. The modified microorganisms of this invention are particularly suitable for preparing such compositions because the bg11 gene can be deleted leaving the remaining CBH and EG components thereby resulting in color restoration and improved softening benefits in the composition without degradative effects.

The detergent compositions of this invention may employ, besides the cellulase composition (deleted in β-glucosidase), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. For a more thorough discussion, see U.S. Application Ser. No. 07/593,919 entitled "*Trichoderma reesei* Containing Deleted Cellulase Genes and Detergent Compositions Containing Cellulases Derived Therefrom", and U.S. Ser. No. 07/770,049, filed Oct. 4, 1991 and entitled "*Trichoderma reesei* Containing Deleted and/or enriched Cellulase and other enzyme Genes and Cellulase Compositions Derived Therefrom" both of which are incorporated herein by reference in their entirety.

In yet another embodiment, the detergent compositions can also contain enhanced levels of β-glucosidase or altered β-glucosidase. In this regard, it really depends upon the type of product one desires to use in detergent compositions to give the appropriate effects.

Preferably the cellulase compositions are employed from about 0.00005 weight percent to about 5 weight percent relative to the total detergent composition. More preferably, the cellulase compositions are employed from about 0.01 weight percent to about 5 weight percent relative to the total detergent composition and even more preferably, from about 0.05 to about 2 weight percent relative to the total detergent composition.

Deletion of the bg11 gene would also provide accumulation of cellooligosaccharides (e.g., cellobiose) in cellolosic solutions treated with cellulase system, which can be purified therefrom. In this regard, the present invention presents the possibility to isolate cellooligosaccharides employing microorganisms in an easy and effective manner.

Cellooligosaccharides are useful in assaying cellulase enzymes for enzymatic activity and are also useful in the synthesis of ethanol and glucose. Moreover, it is contemplated that such oligosaccharides would also be useful as food additives, chemical intermediates, etc.

Heretofore, the use of cellulase containing β-glucosidase to prepare cellooligosaccharides required the deactivation of β-glucosidase by adjusting the pH of the solution to less than about 4 and generally to around 3.8. At this pH, the β-glucosidase is generally inactivated. However, at this pH, the other enzyme components of cellulase are generally less active as compared to their optimum pHs and, accordingly, such a reduction of pH to inactivate the β-glucosidase necessarily results in a less efficient process.

On the other hand, the use of cellulase compositions free of β-glucosidase as per this invention provides a facile means for preparing cellooligosaccharides at a pH of from about 4.5 to about 8; preferably at a pH of from about 4.5 to about 6 and most preferably at the pH optimum for the cellulase composition employed. In this embodiment, the invention is directed to a process for producing cellooligosaccharides which comprises contacting cellulose containing materials (i.e., materials containing at least 20% cellulose and preferably at least 50% cellulose) with a cellulase composition free of β-glucosidase at a pH of from about 4.5 to about 8. Additionally, cellulase compositions containing reduced amounts of β-glucosidase can be obtained by mixing the cellulase produced by a β-glucosidic filamentous fungi and the cellulase produced by a β-glucosidic filamentous fungi which has been modified to be incapable of producing β-glucosidase.

Moreover, the present invention also contemplates the use of the β-glucosidase nucleotide sequence of *T. reesei* to design various probes for the identification of the extracellular β-glucosidase gene in other filamentous fungi. In this regard, the entire nucleotide sequence of the bg11 gene can be used or a portion thereof to identify and clone out the equivalent genes from other filamentous fungi. The sources of filamentous fungi include those fungi from the genus Trichoderma, Aspergillus, Neurospora, Humicola, Penicillium and the like. More particularly, the preferred species include *Trichoderma reesei, Trichoderma viridae, Aspergillus niger, Aspergillus oryzae, Neurospora crassa, Humicola arisea, Humicola insolens, Penicillium pinophilum, Penicillium oxalicum, Aspergillus phoenicis, Trichoderma koningii* and the like. Due to the species homology of the bg11 gene, filamentous fungi equivalent genes are easily identified and cloned. Indicative of this are FIGS. 10A and 10B which illustrate autoradiograph of *A. nidulans* and *N. crassa* (FIG. 10A) and *H. grisea* (FIG. 10B) DNA digested with Hind III and Eco RI and further were blotted and probed with a 2 labeled Hind III 6.0 kb bg11 DNA fragment containing the bg11 gene of *T. reesei*. These autoradiographs clearly illustrate that a DNA fragment containing the bg11 gene of *T. reesei* can be used to identify the extracellular bg11 gene in other fungi.

Thus the bg11 gene of other filamentous fungi may be cloned by the methods outlined above using the $P^{32}$ labelled *T. reesei* bg11 gene as a probe. Once the genes of other filamentous fungi are cloned, they can be used to transform the filamentous fungi from which the gene was derived or other filamentous fungi to overproduce β-glucosidase by the methods described above. Alternatively, the cloned bg11 genes from the other filamentous fungi can be used by the methods described above to delete or disrupt the bg11 gene in the genome of the filamentous fungi from which the bg11 gene was originally cloned.

In order to further illustrate the present invention and advantages thereof, the following specific examples are given, it being understood that the same are intended only as illustrative and in nowise limitative.

EXAMPLE 1

Isolation of Total RNA from *Trichoderma reesei*

A *Trichoderma reesei* culture which over produces cellulases was specifically induced for cellulase using sophorose, a β,1–2 diglucoside as described by Gritzali, 1977. The starting strain of *Trichoderma reesei* is a cellulase over-production strain (RL-P37) developed by mutagenesis by the methods described by Sheir-Neiss, G. and Montenecourt, B. S., *Appl. Microbiol. Biotechnol.*, Vol. 20 (1984) pp. 46–53. A mycelial inoculum of *T. reesei*, from growth on potato dextrose agar (Difco), was added into 50 ml of Trichoderma basal medium containing 1.40 grams/liter $(NH_4)_2SO_4$, 2.0 grams/liter $KH_2PO_4$, 0.30 grams/liter $MgSO_4$, 0.30 grams/liter urea, 7.50 grams/liter BactoPeptone, 5.0 ml/liter, 10% Tween—80, 1.0 ml/liter trace elements-EFG, pH 5.4, which was filtered through a 0.2 micron filter in a 250 ml baffled flask. This culture was incubated at 30° C. for 48 hours with vigorous aeration. Five milliliter aliquots were taken from the culture and added to 25 ml of fresh basal medium in seven 250 ml flasks. These were subsequently grown for 24 hours at 30° C. All cultures were centrifuged in a benchtop clinical centrifuge at 2400× for 10 minutes. The mycelial pellets were washed three times in 50 mls of 17 mM $KHPO_4$ buffer (pH 6.0). Lastly, the mycelia were suspended in six flasks containing 50 ml of 17 mM $KHPO_4$ buffer with the addition of 1 mM sophorose and a control flask containing no sophorose. The flasks were incubated for 18 hours at 30° C. prior to harvesting by filtration through Mira-cloth (Calbiochem). The excess medium was then squeezed out and the mycelial mat was placed directly into liquid nitrogen and may be stored at −70° C. for up to one month. The frozen hyphae were then ground in an electric coffee grinder that was prechilled with a few chips of dry ice until a fine powder was obtained. The powder was then added to about 20 ml of an extraction buffer containing 9.6 grams of p-aminosalicylic acid dissolved in 80 ml of DEP-treated water, 1.6 grams of triiso-propylnaphthalene sulfonic acid dissolved in 80 ml of DEP-treated water, 24.2 grams Tris-HCl, 14.6 grams NaCl, 19.09 grams EDTA, which was diluted to 200 ml total volume with DEP-treated water and the pH was adjusted to 8.5 with NaOH. After addition of the extraction buffer, 0.5 volumes of TE-saturated phenol was also added thereto, and the extraction mixture was placed on ice. One quarter volume of chloroform was then added to the extraction mixture, and the mixture was shaken for two minutes. The phases were then separated by centrifugation at 2500 rpm. The aqueous phase was removed and placed in a centrifuge tube, which contained a few drops of phenol in the bottom of said tube. The tube was placed on ice. The organic phase was then reextracted with 2.0 ml of extraction buffer and placed in a 68° C. water bath for 5 minutes to release the RNA trapped in polysomes and at the interface of the extraction mixture. The extracted mixture was then centrifuged, and the aqueous phase removed and pooled with the other aqueous fraction.

The entire aqueous fractions were then extracted with phenol-chloroform (1:1 v/v) for 4 to 5 times until there was no longer any protein seen visually at the interface. Then 0.1 volume of 3 M sodium acetate, pH 5.2 (made with DEP water and autoclaved) and 2.5 volumes of 95% was added to the organic extracts, and the extracts were frozen at −20° C. for 2 to 3 hours. Alternatively, the RNA was precipitated using 2 M lithium acetate. The RNA was then pelleted by centrifugation at 12,000 rpm for 20 minutes. The pelleted RNA was then resuspended in DEP-water with an RNase inhibitor to a final concentration of 1 unit per pl. To determine whether the genes encoding the enzymes were being induced, total RNA was analyzed.

Analysis of Total RNA Preparation

To confirm whether the genes encoding the enzymes of the cellulase complex were being induced, total RNA was analyzed by Northern blotting as described by Sambrook et al, supra using a 2 fragment of the *T. reesei* cbh2 gene as a probe. The cbh2 clone was isolated using the methods described by Chen et al in "Nucleotide Sequence and Deduced Primary Structure of Cellobio-hydrolase II from *Trichoderma reesei*", *Biotechnology*, Vol. 5 (March 1987), incorporated herein by reference. Site directed mutagenesis (Sambrook et al., supra) was performed on the cbh2 clone and a Bgl II site was placed at the exact 5' end of the opening reading frame and an Nhe I site at the exact 3' end. The Bgl II/Nhe I coding sequence was then cloned into a pUC218 phagemid. For use as a probe, the cbh2 fragment was digested with Bgl II/Nhe I and isolated by gel electrophoresis. The results indicated that the level of cbh2 specific mRNA reached a peak at 14–18 hours post induction. The total RNA from 14, 18 and 22 hours was then pooled.

EXAMPLE 2

Purification of Polvadenylated mRNA mRNA was then isolated from the pooled fraction of total RNA set forth above using oligo (dT) cellulose chromatography. Oligo(dT) cellulose (type 3 from Collaborative Research, Lexington, Mass.) is first equilibrated with oligo (dT) binding buffer containing 0.01 M Tris-HCl, pH 7.5, 0.5 M NaCl, and 1 mM EDTA, then aliquots of 25–300 mg were added to 1.5 ml microfuge tubes. RNA dissolved in 1 ml of binding buffer was added and allowed to bind for 15 min. with gentle shaking. The suspensions were centrifuged at 1500 g for 3–5 min., washed 3–5 times with 1 ml of binding buffer, and then washed 3 times with 400 $\mu$l of elution buffer containing 0.01 M Tris-HCl, pH 7.5, and 1 mM EDTA. The eluates were pooled, readjusted to 0.5 M NaCl, rebound, and reeluted with three washes of elution buffer. The final three elution buffer washes were pooled and mRNA was recovered by ethanol precipitation.

Analysis of Total RNA and polyadenylated mRNA

Total RNA and the polyadenylated RNA were fractionated on 1% formaldehyde-agarose gels using 10 $\mu$g of RNA for each lane, blotted to Nytran$^R$ membranes and analyzed by the Northern blot method described by Thomas in "Hybridization of denatured RNA and Small DNA fragments transferred to Nitrocellulose", *Proc. Natl. Acad. Sci. USA*, Vol. 77 (1980), pp. 5201–5205.

Briefly, this procedure involves denaturing RNA (up to 10 $\mu$g/8 $\mu$l reaction) by incubation in 1 M glyoxal/50% (vol/vol) Me$_2$SO/10 mM sodium phosphate buffer, pH 7.0 at 50° C. for 1 hr. The reaction mixture was cooled on ice and 2 $\mu$l of sample buffer containing 50% (vol/vol) glycerol, 10 mM sodium phosphate buffer at 7.0 and bromophenol blue was added. The samples were electro-phoresed on horizontal 1% formaldehyde-agarose gels in 10 mM phosphate buffer, pH 7.0 at 90 v for 6 hours.

The glyoxylated RNA was transferred from agarose gels to nitrocellulose by using 3 M NaCl/0.3 M trisodium citrate (20X NaCl/cit). After electrophoresis, the gel was placed over two sheets of Whatman 3 MM paper which was saturated with 20X NaCl/cit. Nitran$^R$ membrane was wetted with water, equilibrated with 20X NaCl/cit and laid over the gel. The gel was then covered with two sheets of Whatman 3 MM paper and a 5 to 7 cm layer of paper towels, a glass plate and a weight. Transfer of the RNA was completed in 12–15 hours. The blots were then dried under a lamp and baked in a vacuum for over 2 hrs. at 80° C.

The membranes were probed with a cbh2 probe to verify that the polyadenylated MRNA pool contained cbh2 mRNA and by inference the genes encoding the enzymes of the cellulase complex were indeed induced.

EXAMPLE 3

Synthesis of cDNA

A. First Strand Synthesis

Synthesis of cDNA was performed using the BRL cDNA Synthesis System$^R$ (Bethesda Research Laboratories, Md.) according to the instructions of the manufacturer. To a sterile, DEPC-treated tube in ice was added 10 μl of 5X First Strand Buffer containing 250 mM Tris-HCl, pH 8.3, 375 mM KCl, 15 mM MgCl$_2$, 50 mM DTT, 2.5 μl 10 mM dNTP Mix (10 mM DATP, 10 mM dCTP, 10 mM dGTP, 10 mM dTTP), 5 μl Oligo (dT)$_{12-18}$ (0.5) mg/ml), 10 μl of mRNA at 0.5 mg/ml and 20 μl diethylpirocarbmate(DEPC)-treated water to create a final composition containing 50 mM Tris-HCl (pH 8.3), 75 mM KCl, 3 mM MgCl$_2$, 10 mM dithiothreitol, 500 μM each DATP, dCTP, dGTP and dTTP, 50 μg/ml Oligo (dT)$_{12-18}$, 100 μg/ml polyadenylated RNA and 10,000 U/ml cloned M-MLV reverse transcriptase. A control run was also run simultaneously using 10 μl of a 2.3 kb control RNA (0.5 mg/ml) in lieu of the mRNA.

The reaction was initiated by adding 2.5 μl of Molony murine leukemia virus (M-MLV) reverse transcriptase (100 Units/μl) to the MRNA tube and the control RNA. The samples were mixed. All reaction tubes were incubated at 37° C. for one hour and then placed on ice.

A small aliquot from the reaction mixture was run on a gel to confirm its presence and quantity. The yield obtained was about 2–6 μg.

B. Second Strand Synthesis

To the control tube on ice after first strand synthesis was added 230.6 μl DEPC-treated water, 6 μl 10 mM dNTP mix, 32 μl 10X second strand buffer containing 188 mM Tris-HCl, pH 8.3, 906 mM KCl, 100 mM (NH$_4$)$_2$ SO$_4$, 46 MM MgCl$_2$, 37.5 mM dithiothreitol, 1.5 mM NAD, 8 μl *E. coli* DNA Polymerase I (10 μ/μl), 1.4 μl *E. coli* RNase H and 1 μl *E. coli* DNA ligase (100 units).

To the first strand synthesis of the sample was added on ice 289.5 μl of DEPC-treated water, 7.5 μl 10 mM dNTP mix, 40 μl 10X second strand buffer, 10 μl *E. coli* DNA Polymerase I, 1.75 μl *E. coli* RNaseH and 1.25 *E. coli* DNA ligase, to create a final composition containing 25 mM Tris-HCl (pH 8.3), 100 mM KCl, 10 mM (NH$_4$)$_2$SO$_4$, 5 mM MgCl$_2$, 250 μM each dATP, dCTP, dGTP, dTTP, 0.15 mM NAD, 5 mM Dithiothreitol, 250 U/ml DNA Polymerase I, 8.5 U/ml RNase H, and 30 U/ml DNA Ligase. Both the control tube and the sample tube were vortexed gently and incubated for 2 hours at 16° C. After incubation, both tubes were placed on ice.

The sample tube was then extracted with 415 μl of phenol and ethanol precipitated. The pellet was dissolved in 200 μl of sterile TE buffer (10 mM Tris-HCl pH 7.5, 1 mM Na$_2$EDTA) and reprecipitated from 7.5 M ammonium acetate with ethanol.

An aliquot of the sample was further analyzed by gel electrophoresis to check for purity. The yield of the synthesis was about 4.0 μg.

The remaining control sample was further extracted with phenol and ethanol precipitated as described above for the sample. After dissolving the pellet in 200 μl of sterile TE buffer, reprecipitating the sample from ammonium acetate with ethanol, and redissolving the dry pellet in 20 μl of sterile TE buffer, 2 μl of the solution was then further analyzed by gel electrophoresis to check for purity.

EXAMPLE 4

Amplification of bg11 cDNA Sequences

Amplification of the cDNA fragments encoding a portion of the *T. reesei* β-glucosidase gene, bg11, was performed using the polymerase chain reaction (PCR) method with Taq$^R$ polymerase and a Perkin Elmer Cetus Thermal Cycler$^R$.

The reaction mixture was formed by mixing 76 μl deionized water, 10 μl of a 10X mixture of buffer containing 166 mM (NH$_4$)$_2$ SO$_4$, 670 mM Tris-HCl, pH 8.8, 67 mM MgCl$_2$, 67 μm EDTA, 10 mM β-mercaptoethanol, 10 μl dimethylsulfoxide and 1.7 mg/ml BSA diluted to a total volume of 1.0 ml with deionized water, 8 μl of 2 dNTPs (each), 1 μl 5' oligonucleotide primer, 1 μl 3' internal oligonucleotide primer, 1.0 μg cDNA diluted in 3 μl deionized water, and 1 μg Taq$^R$ polymerase.

The amplification method consists of an initial denaturing cycle at 95° C. for 10 minutes, followed by a two minute annealing step at 50° C. and a 10 minute polymerization cycle at 65° C., for an additional 30 cycles.

A. Oligonucleotide Primers

The oligonucleotide primers used to amplify the cDNA fragment encoding the *T. reesei* bg11 gene were designed based on the degeneracy of the genetic code for the selected amino acids for an N terminal region of the bg11 gene and an internal oligonucleotide. The 5' oligonucleotide primer consisted of the sequence:

5' GCI GTI CCT CCT GCI GG 3'(SEQ ID NO:3)

wherein I=inosine.

The internal 3' oligonucleotide primer consisted of a pool of 16×21 oligonucleotides. This pool was based on various derivations of the following sequences:

5' GTT G/ATT ICC G/ATT G/AAA G/ATC TGT 3'(SEQ ID NO:4)

EXAMPLE 5

Subcloning of PCR Generated Fragments

Ninety μl of each reaction mix was fractionated on 4% polyacrylamide gels in 1X TBE, the major band was excised and eluted from the gel slice as described by Sambrook et al, supra. The eluted DNA fragment was precipitated in ethanol and resuspended in 15 μl of TE buffer (10 mM Tris, 1 mM EDTA). Each 1–2 μg DNA fragment was then treated with 0.5 mM ATP and T$_4$ polynucleotide kinase to phosphorylate the 5' end of each fragment following by the procedures of Sambrook et al, supra. Blunt ends were generated by adding 3 μl of 10X T$_4$ polynerase buffer (330 mM Tris-acetate at pH 7.9, 660 mM potassium acetate, 100 mM magnesium acetate, 1 μl of 2.5 mM dNTPS, 1 μl of T$_4$ DNA polymerase and 5 μl of distilled water). The blunt-end reaction mixture was then incubated at 37° for 60 minutes. The reaction was stopped by addition of EDTA to a final concentration of 1 mM EDTA and the sample was further heated for 10 minutes at 65° C.

The blunt-end DNA fragments were then ligated with SmaI cleaved and dephosphorylated pUC218 which had been infected with M13X07 as described by Sambrook et al, supra. The cloning vectors pUC218 and pUC219 were derived from pUC118 and pUC119 by insertion of the Bgl II, Cla I and Xho I polylinker as described by Korman et al in "Cloning, Characterization, and expression of two α-amylase genes from *Aspergillus niger* var. *awamori*", *Current Genetics*, Vol. 17, pp. 203–212, (1990).

The aforedescribed phagemid was then used to transform *E. coli* strain JM101 as described by Yarnisch et al in "Improved M13 phage cloning vectors and host strains: nucleotide sequence of the M13mp18 and pUC19 Vectors" *Gene*, Vol. 1197, pp. 103–119 (1985).

EXAMPLE 6

Isolation of cDNA Subcloned Fragment

The transformed strain was inoculated in 1.5 ml of 2YT broth in a tube which had been previously inoculated with 15

μl of saturated *E. coli* JM101. The culture was grown for 8 hours under shaking at 37° C.

The culture mixture was then spun at 6000 rpm for 5 minutes, and the supernatant was poured off into another tube. To the supernatant 300 μl of 2.5 M NaCl, 20% PEG was added, and the solution was mixed. The mixture was then incubated at room temperature for 15 minutes.

The solution was then spun for 5 minutes in a microfuge, and the supernatant was aspirated off. The solution was vortexed once again, and the supernatant was further aspirated off. 100 μl of equilibrated phenol was added to the tube, and the tube was vortexed. 100 μl of chloroform was added, and once again the tube was vortexed. The tube was heated at 55° C. for 5 minutes, mixed, and microfuged an additional 5 minutes. 160 μl of the supernatant was then pipetted off and transferred to a clear tube. 20 μl of iN NaOAC, pH 4.5, and 400 μl of 95% ETOH were added to the supernatant, and the solution was mixed and frozen on dry ice for 5 minutes. The tube was then spun for an additional 15 minutes, and the supernatant was aspirated off.

1000 μl of 70% ethanol was added to the tube, and the tube was spun for an additional 2 minutes and reaspirated. The mixture was spun once more under vacuum for 4 minutes, and the pellet was resuspended in 15 pl TE buffer.

EXAMPLE 7

Determination of the Nucleotide Sequence of 700 bp cDNA fragment

The nucleotide sequence of the 700 bp cDNA fragment was determined using the dideoxy DNA sequencing method described by Sanger et al, "DNA Sequencing with chain terminating inhibitors", *Proc. Natl. Acad. Sci. U.S.A.*, Vol. 74 (1977), p. 5463, using the Sequenase$^R$ reagent kit (U.S. Biochemicals).

EXAMPLE 8

Analysis of bg11 gene
A. Sequence Analysis
Nucleotide sequencing was done by the dideoxy chain termination method of Sanger et al (1977) using the Sequenase$^R$ reagent kit (U.S. Biochemicals).
B. Amino Acid Sequencing
A 2.5-nmol sample of the reduced and carboxymethylated β-glucosidase preparation purified (per Chirico and Brown, European Journal of Biochem., Vol. 165, pp. 333 et seq.) was subjected to N-terminal sequencing on a proprietary multiphase sequencer.

To a sample of β-glucosidase, Endo-Lys C protease was added to 1% of the total protein and the mixture incubated for 1 hour at 37° C. or the protein sample was subject to cyanogen bromide treatment. An equal volume of HPLC solution A (0.05% TEA/0.05% TFA in water) was added to stop the reaction. The resulting CNBr and Endo-Lys C fragments were separated by chromatography on a Brownlee C-4 column using a linear gradient of 0–100% HPLC solution B (0.05% TEA/0.05% TFA in n-propanol) at a rate of 1% per minute. Several peaks were collected for amino acid sequencing and the data are denoted in FIG. 1.

EXAMPLE 9

Identification of bg11 gene from *T. reesei*

The 700 bp bg11 cDNA fragment was then labelled with $^{32}$P using methods described by Sambrook et al, supra.

Genomic DNA from *T. reesei* was prepared by filtering a 24–36 hour culture of *T. reesei* through Miracloth and freezing the mycelia obtained from the culture medium. The frozen mycelia were then ground into a fine powder and 22 mls of TE, and 4 mls of 20% SDS were added to the powdered mycelia and mixed. 10 ml of phenol and chloroform was added to the mixture prior to centrifugation and removal of the aqueous phase. 200 μl of 5 mg/ml proteinase K was added to the organic extract, and the mixture was incubated for 20 minutes at 55° C. The DNA was then further extracted by methods known in the art using chloroform/phenol extraction followed by ethanol precipitation. The isolated DNA was then treated with 1 μg of heated ribonuclease A (100° C. for 15 minutes) per 20 μg of genomic DNA in TE buffer at 37° C. for 30 minutes, then cooled to room temperature. The genomic DNA from *T. reesei* was then cut singly or in combination with a variety of restriction enzymes such as Eco RI, Hind III and the like, Southern blotted and hybridized with the P$^{32}$ labelled 700 bp cDNA fragment of the bg11 gene as a probe. From this analysis it was determined that Hind III was the restriction enzyme of choice used to locate the β-glucosidase gene.

10 to 20 units of Hind III per milligram of genomic DNA was added to the DNA and then the DNA was extracted with phenol-chloroform to remove protein. The treated DNA was then alcohol precipitation and resuspended to 2 grams/liter in TE buffer.

4 μl samples from the Hind III digestion of genomic DNA were loaded on a 1% agarose gel and fractionated electrophoretically. The gel was then Southern blotted and probed with the P$^{32}$ 700 bp cDNA probe. A 6.0 kb band was identified on the Southern blot of Hind III digested genomic DNA from *T. reesei*.

The remaining Hind III genomic DNA was then subjected to a preparative gel electrophoresis and fragments ranging from 5 kb to 7 kb were then electroeluted from the agarose gel and cloned into Hind III digested pUC218. The resulting plasmids were used to transform *E. coli* JM101 to create a library. Then the library was screened by colony hybridization using P$^{32}$ labelled 700 bp bg11 cDNA as a probe to identify those colonies containing DNA coding for the bg11 gene.

The positive colonies from the transformation were then picked and the DNA isolated therefrom by phenol:chloroform extraction and ethanol precipitation, described by Sambrook et al, supra.

The isolated DNA from the positive colonies was digested both singly and in various combinations with the following restriction enzymes: Hind III, Eco RI, Sst 1, Kpn I, Bam HI, Xho 1, Bgl II, Cla I, Xba I, Sal I, Pst I, Sph I, Bal I, and Pvu II. The digestions were subjected to agarose gel electrophoresis, and the resultant banding pattern was used to construct a restriction map of the cloned 6.0 kb genomic DNA. The same agarose gel was Southern blotted and probed with the P$^{32}$ labelled 700 bp bg11 cDNA to identify which genomic restriction fragments shared homology with the bg11 cDNA. The mapping experiments confirmed that the entire bg11 gene is contained on the genomic Hind III clone. Pvu II and Bal I restriction fragments which ranged in size from 600 bp to 1500 bp hybridized with the 700 bp DNA bg11 clone and were chosen for subcloning into pUC218 phagemid. After cloning these fragments into the phagemid, the Pvu II and Bal I subclones were then sequenced using the dideoxy chain termination method of Sanger et al (1977). It was then determined from this sequencing that the overlapping sequences of the subclones aligned with a single contiguous sequence totaling 3033 bp within which the nucleotide sequence was determined on both strands.

EXAMPLE 10

Construction of pSASβ-glu

The starting vector for the construction of pSASβ-glu was the plasmid pSAS. pSAS was constructed in the following way. pUC100 (a commercially available plasmid vector) was digested with the restriction enzyme SmaI and the 5' phosphate groups subsequently removed by digestion with calf intestinal alkaline phosphatase. The linear vector fragment was purified from undigested vector and protein by agarose gel electrophoresis followed by isolation of the linear vector DNA from the isolated gel slice by electroelution. The amdS gene was isolated as a 2.4 kb SstI restriction fragment following separation from the vector sequences (contained in—Hynes, M. J., Corrick, C. M., and King, J. A., "Isolation of genomic clones containing the amdS gene of *Aspergillus nidulans* and their use in the analysis of structural and regulatory mutations", *Mol. Cell. Biol.*, Vol. 3 (1983), pp. 1430–1439). The 2.4 kb SstI amdS fragment and the 2.7 kb pUC100 vector fragment were then ligated together (Sambrook et al., supra) and the ligation mix transformed and propagated in the *E. coli* host strain, JM101.

pSASβ-glu was constructed by digesting pSAS with the restriction enzyme Hind III, and purifying the linear fragment as described above. Into this Hind III treated pSAS vector fragment was ligated a 6.0 kb Hind III fragment of *T. reesei* genomic DNA that contained all of the coding region of the bg11 gene along with sequences necessary for the genes transcription and translation.

EXAMPLE 11

Preparation of BGL1 Deletion yector

The gene replacement vector pUCΔβ-Glu A/R pyr, illustrated in FIG. 3B, was constructed by cloning a 6.0 kb genomic HindIII fragment, known to contain the entire bg11 gene, into the polylinker of pUC218 which had been cut with HindIII and the ends dephosphorylated with calf intestinal alkaline phosphatase. The coding region for the bg11 gene was then removed from this plasmid by digesting the plasmid with ApaI and EcoRV at unique ApaI and EcoRV restriction sites situated at the very 5' and 3' end of the bg11 open reading frame and isolating the linear plasmid DNA. The restriction site ends were made blunt with T4 DNA polymerase. This plasmid was then ligated with an isolated 2412 bp Hind III/Bam HI restriction fragment containing the pyrG gene from *Aspergillus niger* (Hartingsreldt et al., Mol. Gen. Genet. 206:71–75 (1987) in which the restriction ends were made blunt by treatment with T4 DNA polymerase to create pUCΔβGlu A/R pyr (FIG. 3B).

EXAMPLE 12

Isolation of Protoplasts

Mycelium was obtained by inoculating 100 ml of YEG (0.5% yeast extract, 2% glucose) in a 500 ml flask with about 5×10[7] *T. reesei* cells. The flask was then incubated at 37° C. with shaking for about 16 hours. The mycelium was harvested by centrifugation at 2,750×g. The harvested mycelium were further washed in 1.2 M sorbitol solution and resuspended in 40 ml of Novozymt, which is the tradename for a multi-component enzyme system containing 1,3-alpha-glucanase, 1,3-beta-glucanase, laminarinase, xylanase, chitinase and protease from Novo Biolabs, Danbury, Conn., solution containing 5 mg/ml Novozym[R] 234; 5 mg/ml $MgSO_4.7H_2O$; 0.5 mg/ml bovine serum albumin; 1.2 M sorbitol. The protoplasts were removed from cellular debris by filtration through Miracloth (Calbiochem Corp.) and collected by centrifugation at 2,000×g. The protoplasts were washed three times in 1.2 M sorbitol and once in 1.2 M sorbitol, 50 mM $CaCl_2$, centrifuged and resuspended. The protoplasts were finally resuspended at a density of 2×10[8] protoplasts per ml of 1.2 M sorbitol, 50 mM $CaCl_2$.

EXAMPLE 13

Transformation of Fungal Protoplasts with pSASβ-glu

200 μl of the protoplast suspension prepared in Example 12 was added to 20 μl (20 μg) of pSASβ-glu in TE buffer (10 mM Tris, pH 7.4; 1 mM EDTA) and 50 μl of a polyethylene glycol (PEG) solution containing 25% PEG 4000, 0.6 M KCl and 50 mM $CaCl_2$. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2 M sorbitol and 50 mM $CaCl_2$ was added thereto and this solution was further mixed. The protoplast solution was then immediately added to molten aliquot's of Vogels Medium N (3 grams sodium citrate, 5 grams $KH_2PO_4$, 2 grams $NH_4NO_3$, 0.2 grams $MgSO_4.7H_2O$, 0.1 gram $CaCl_2.2H_2O$, 5 μg α-biotin, 5 mg citric acid, 5 mg $ZnSO_4.7H_2O$, 1 mg $Fe(NH_4)_2.6H_2O$, 0.25 mg $CuSO_4.5H_2O$, 50 μg $MnSO_4.4H$ containing an additional 1% glucose, 1.2 M sorbitol and 1% agarose. The protoplast/medium mixture was then poured onto a solid medium containing the same Vogel's medium as stated above containing in addition acetamide as a nitrogen source. Since *T. reesei* does not contain a functional equivalent to the amdS gene only transformants will grow on this medium. These colonies were subsequently transferred and purified on a solid Vogel's medium N containing as an additive, 1% glucose. The bg11 gene inserted transformant strain is called A83pSASβGlu.

Stable transformants can be distinguished from unstable transformants by their faster growth rate and the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

FIG. 6 is an autoradiograph of a Southern blot using the $P^{32}$ labelled 700 bp fragment as a probe, of the different transformants with enhanced copies of the bg11 gene using genomic *T. reesei* from an overproducing strain digested with Hind III as a control. This autoradiograph clearly shows that the transformants contained enhanced amount of the bg11 gene compared with the control.

FIG. 4 is an autoradiograph of a Northerr blot of RNA isolated from one of the transformed strains produced by the present invention following induction with soporose illustrating a corresponding increase in the levels of bg11 message when compared to the parental strain of *T. reesei*.

Besides visual analysis of the transformants, quantitative analysis was also completed by cutting the appropriate bands out of the Nytran[R] membrane and counting the radioactive label present therein in a scintillation counter. This experiment was performed to obtain a more precise estimate of the relative amounts of message as shown in Table III below:

TABLE III

| CPM | Parental *Trichoderma reesei* strain | Transformed *Trichoderma reesei* strain |
|---|---|---|
| CPM β-glu message | 14.4 | 25.4 |
| CPM CBHII | 227.1 | 95.2 |
| CPM β-glu/ CBHII | 0.0634 | 0.2668 |

Table III illustrates that the transformant produced by the process of the present invention has extra β-glucosidase MRNA and hence an increase in β-glucosidase enzyme resulting in an increase in specific activity.

EXAMPLE 14

Transformation of Fungal Protoplasts with pUCΔβGlu A/R pvr4

Mutants of *T. reesei* lacking the coding sequence for the extracellular β-glucosidase gene, bglI, were obtained by a targeted gene replacement event. pUCΔβGlu A/R pyr4 plasmid was digested with Hind III to obtain a linear HindIII fragment in which the bg11 coding sequences were replaced with the pvrG gene from *Asperaillus niger*. Protoplasts were transformed with the linear DNA fragment containing the bg11 flanking sequences and the pyr4 by the methods of Examples 12 and 13. The deletion transformants were called Δ12 and Δ36. After transformation, the protoplast solution was then added to molten aliquots of Vogel's Medium N containing an additional 1% glucose, 1.2 M sorbitol and 1% agarose. The protoplast/mdium mixture was then pourred into a solid medium containing the same Vogel's medium N. No uridine was present in the medium and therefore only transformed colonies were able to grow as a result of complementation of the pvr4 mutation of the *T. reesei* strain RL-P37 by the wild type pyr4 gene inserted in the DNA fragment. Stable transformants were then selected by the method recited in Example 13.

EXAMPLE 15

Analysis of the Transformants

The transformants were analyzed for the presence or absence of the bg11 gene using the 700 bp cDNA probe recited above. The transformants were digested using HindIII. Total genomic DNA from selected transformants was digested with HindIII restriction enzyme, run on a 1% agarose gel, transferred to NitranR membrane and probed with a 2 labelled 700 bp cDNA rectied above and visualized by autoradiography on X-ray film. The results of this analysis are set forth in FIG. 5A illustrate that the transformants (Δ12 and Δ36) did not contain a band corresponding to the bg11 gene whereas the wild type strain (RL-P37, i.e., P-37) did.

mRNA isolated from the transformants of Example 14 and analyzed on a Northern blot, as in Example 2. As indicated in FIG. 5B, Northern blot analysis using the $P^{32}$ labelled 2.2 Kb ApaI/EcoRV bg11 probe indicated that bg11 specific mRNA was present in *T. resei* RL-P37 pyrG69 and is absent in the transformants Δ12 and Δ36.

Protein was recovered as per Example 8 above and then analyzed for the presence of β-glucosidase by use of polyclonal antibodies (from rabbits challenged with pure β-glucosidase) tagged with horseradish peroxidase to permit detection. The antibodies were used to identify pure β-glucosidase (100 ng—Column A; 1000 ng—Column B); cellulase produced from wild type *T. reesei* (Column C); and from cellulase produced by a *T. reesei* strain genetically engineered to delete the β-glucoidase gene (Column D). The results of this analysis are set forth in FIG. 5C and show that only Column D did not contain β-glucosidase.

While the invention has been described in terms of various preferred embodiments, the skilled artisan will appreciate that various modifications, substitutions, omissions, and changes may be made without departing from the scope thereof. Accordingly, it is intended that the scope of the present invention be limited solely by the scope of the following claims, including equivalents thereof.

What is claimed is:

1. A method of detecting DNA encoding a β-glucosidase from a filamentous fungus comprising the steps of:
   a) contacting DNA of a filamentous fungus with a nucleic acid comprising SEQ ID NO:1, or a portion thereof that specifically hybridizes to DNA encoding β-glucosidase under hybridizing conditions; and
   b) detecting hybridized DNA.

2. The method of claim 1, wherein said filamentous fungus is selected from the group consisting of Aspergillus, Neurospora, Humicola, Trichoderma or Penicillium.

3. The method of claim 2, wherein said filamentous fungus is selected from the group consisting of *Trichoderma reesei, Trichoderma viridae, Aspergillus niger, Aspergillus oryzae, Neurospora crassa, Humicola grisea, Humicola insolens, Penicillium pinophilum, Penicillium oxalicum, Aspergillus phoenicis* or *Trichoderma konigii*.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3033 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:

(A) ORGANISM: Trichoderma reesei (ix) FEATURE:
        (A) NAME/KEY: CDS
        (B) LOCATION: join(311..375, 446..2205, 2270..2679)

(ix) FEATURE:
        (A) NAME/KEY: intron
        (B) LOCATION: 376..445

(ix) FEATURE:
        (A) NAME/KEY: intron
        (B) LOCATION: 2206..2269

(xi) SEQUENCE DESCRIPTION: SEQ ID NO:1:

```
TGGCCACAGA GGGAGAGTTC GCGCTACCGC TTGGTCGAGG AAATGATCGC CCACGGCCTC      60

AAATCGTAAA TCTCGGTGTG GGTAGGAGTG CAACGATGGG ATTTGGCCGC AATGCTGCCG     120

AGCCCGAGTG TTTCTGCAAC GTTATCCAGG AGATTTGCGC TTGCCCAAGA GGGAGTTGAC     180

GGGGAGAGTC CCAACTGGTT CCTTCAGTAA CGCCACCCTG GCAGACTATA TAACTTGTGG     240

ACAAGACTCT GCTTTGTTGA GTTCTTCCTA CCAGTCTTGA CCAAGACCAT TCTGTTGAGC     300

CCAATCAGAA ATG CGT TAC CGA ACA GCA GCT GCG CTG GCA CTT GCC ACT        349
             Met Arg Tyr Arg Thr Ala Ala Ala Leu Ala Leu Ala Thr
               1               5                  10

GGG CCC TTT GCT AGG GCA GAC AGT  CA GTATAGCTGG TCCATACTGG              395
Gly Pro Phe Ala Arg Ala Asp Ser  His
 15                  20

GATGTGATAT GTATCCTGGA GACACCATGC TGACTCTTGA ATCAAGGTAG C TCA ACA       452
                                                         Ser Thr

TCG GGG GCC TCG GCT GAG GCA GTT GTA CCT CCT GCA GGG ACT CCA TGG       500
Ser Gly Ala Ser Ala Glu Ala Val Val Pro Pro Ala Gly Thr Pro Trp
 25                  30                  35                  40

GGA ACC GCG TAC GAC AAG GCG AAG GCC GCA TTG GCA AAG CTC AAT CTC       548
Gly Thr Ala Tyr Asp Lys Ala Lys Ala Ala Leu Ala Lys Leu Asn Leu
                 45                  50                  55

CAA GAT AAG GTC GGC ATC GTG AGC GGT GTC GGC TGG AAC GGC GGT CCT       596
Gln Asp Lys Val Gly Ile Val Ser Gly Val Gly Trp Asn Gly Gly Pro
             60                  65                  70

TGC GTT GGA AAC ACA TCT CCG GCC TCC AAG ATC AGC TAT CCA TCG CTA       644
Cys Val Gly Asn Thr Ser Pro Ala Ser Lys Ile Ser Tyr Pro Ser Leu
         75                  80                  85

TGC CTT CAA GAC GGA CCC CTC GGT GTT CGA TAC TCG ACA GGC AGC ACA       692
Cys Leu Gln Asp Gly Pro Leu Gly Val Arg Tyr Ser Thr Gly Ser Thr
     90                  95                 100

GCC TTT ACG CCG GGC GTT CAA GCG GCC TCG ACG TGG GAT GTC AAT TTG       740
Ala Phe Thr Pro Gly Val Gln Ala Ala Ser Thr Trp Asp Val Asn Leu
105                 110                 115                 120

ATC CGC GAA CGT GGA CAG TTC ATC GGT GAG GAG GTG AAG GCC TCG GGG       788
Ile Arg Glu Arg Gly Gln Phe Ile Gly Glu Glu Val Lys Ala Ser Gly
                125                 130                 135

ATT CAT GTC ATA CTT GGT CCT GTG GCT GGG CCG CTG GGA AAG ACT CCG       836
Ile His Val Ile Leu Gly Pro Val Ala Gly Pro Leu Gly Lys Thr Pro
            140                 145                 150

CAG GGC GGT CGC AAC TGG GAG GGC TTC GGT GTC GAT CCA TAT CTC ACG       884
Gln Gly Gly Arg Asn Trp Glu Gly Phe Gly Val Asp Pro Tyr Leu Thr
        155                 160                 165

GGC ATT GCC ATG GGT CAA ACC ATC AAC GGC ATC CAG TCG GTA GGC GTG       932
Gly Ile Ala Met Gly Gln Thr Ile Asn Gly Ile Gln Ser Val Gly Val
    170                 175                 180

CAG GCG ACA GCG AAG CAC TAT ATC CTC AAC GAG CAG GAG CTC AAT CGA       980
Gln Ala Thr Ala Lys His Tyr Ile Leu Asn Glu Gln Glu Leu Asn Arg
```

-continued

```
              185                     190                     195                     200
GAA ACC ATT TCG AGC AAC CCA GAT GAC CGA ACT CTC CAT GAG CTG TAT              1028
Glu Thr Ile Ser Ser Asn Pro Asp Asp Arg Thr Leu His Glu Leu Tyr
                    205                     210                     215

ACT TGG CCA TTT GCC GAC GCG GTT CAG GCC AAT GTC GCT TCT GTC ATG              1076
Thr Trp Pro Phe Ala Asp Ala Val Gln Ala Asn Val Ala Ser Val Met
                    220                     225                     230

TGC TCG TAC AAC AAG GTC AAT ACC ACC TGG GCC TGC GAG GAT CAG TAC              1124
Cys Ser Tyr Asn Lys Val Asn Thr Thr Trp Ala Cys Glu Asp Gln Tyr
                    235                     240                     245

ACG CTG CAG ACT GTG CTG AAA GAC CAG CTG GGG TTC CCA GGC TAT GTC              1172
Thr Leu Gln Thr Val Leu Lys Asp Gln Leu Gly Phe Pro Gly Tyr Val
                    250                     255                     260

ATG ACG GAC TGG AAC GCA CAG CAC ACG ACT GTC CAA AGC GCG AAT TCT              1220
Met Thr Asp Trp Asn Ala Gln His Thr Thr Val Gln Ser Ala Asn Ser
265                     270                     275                     280

GGG CTT GAC ATG TCA ATG CCT GGC ACA GAC TTC AAC GGT AAC AAT CGG              1268
Gly Leu Asp Met Ser Met Pro Gly Thr Asp Phe Asn Gly Asn Asn Arg
                    285                     290                     295

CTC TGG GGT CCA GCT CTC ACC AAT GCG GTA AAT AGC AAT CAG GTC CCC              1316
Leu Trp Gly Pro Ala Leu Thr Asn Ala Val Asn Ser Asn Gln Val Pro
                    300                     305                     310

ACG AGC AGA GTC GAC GAT ATG GTG ACT CGT ATC CTC GCC GCA TGG TAC              1364
Thr Ser Arg Val Asp Asp Met Val Thr Arg Ile Leu Ala Ala Trp Tyr
                    315                     320                     325

TTG ACA GGC CAG GAC CAG GCA GGC TAT CCG TCG TTC AAC ATC AGC AGA              1412
Leu Thr Gly Gln Asp Gln Ala Gly Tyr Pro Ser Phe Asn Ile Ser Arg
                    330                     335                     340

AAT GTT CAA GGA AAC CAC AAG ACC AAT GTC AGG GCA ATT GCC AGG GAC              1460
Asn Val Gln Gly Asn His Lys Thr Asn Val Arg Ala Ile Ala Arg Asp
345                     350                     355                     360

GGC ATC GTT CTG CTC AAG AAT GAC GCC AAC ATC CTG CCG CTC AAG AAG              1508
Gly Ile Val Leu Leu Lys Asn Asp Ala Asn Ile Leu Pro Leu Lys Lys
                    365                     370                     375

CCC GCT AGC ATT GCC GTC GTT GGA TCT GCC GCA ATC ATT GGT AAC CAC              1556
Pro Ala Ser Ile Ala Val Val Gly Ser Ala Ala Ile Ile Gly Asn His
                    380                     385                     390

GCC AGA AAC TCG CCC TCG TGC AAC GAC AAA GGC TGC GAC GAC GGG GCC              1604
Ala Arg Asn Ser Pro Ser Cys Asn Asp Lys Gly Cys Asp Asp Gly Ala
                    395                     400                     405

TTG GGC ATG GGT TGG GGT TCC GGC GCC GTC AAC TAT CCG TAC TTC GTC              1652
Leu Gly Met Gly Trp Gly Ser Gly Ala Val Asn Tyr Pro Tyr Phe Val
                    410                     415                     420

GCG CCC TAC GAT GCC ATC AAT ACC AGA GCG TCT TCG CAG GGC ACC CAG              1700
Ala Pro Tyr Asp Ala Ile Asn Thr Arg Ala Ser Ser Gln Gly Thr Gln
425                     430                     435                     440

GTT ACC TTG AGC AAC ACC GAC AAC ACG TCC TCA GGC GCA TCT GCA GCA              1748
Val Thr Leu Ser Asn Thr Asp Asn Thr Ser Ser Gly Ala Ser Ala Ala
                    445                     450                     455

AGA GGA AAG GAC GTC GCC ATC GTC TTC ATC ACC GCC GAC TCG GGT GAA              1796
Arg Gly Lys Asp Val Ala Ile Val Phe Ile Thr Ala Asp Ser Gly Glu
                    460                     465                     470

GGC TAC ATC ACC GTG GAG GGC AAC GCG GGC GAT CGC AAC AAC CTG GAT              1844
Gly Tyr Ile Thr Val Glu Gly Asn Ala Gly Asp Arg Asn Asn Leu Asp
                    475                     480                     485

CCG TGG CAC AAC GGC AAT GCC CTG GTC CAG GCG GTG GCC GGT GCC AAC              1892
Pro Trp His Asn Gly Asn Ala Leu Val Gln Ala Val Ala Gly Ala Asn
                    490                     495                     500

AGC AAC GTC ATT GTT GTT GTC CAC TCC GTT GGC GCC ATC ATT CTG GAG              1940
Ser Asn Val Ile Val Val Val His Ser Val Gly Ala Ile Ile Leu Glu
```

-continued

```
Ser Asn Val Ile Val Val His Ser Val Gly Ala Ile Ile Leu Glu
505                 510                 515                 520

CAG ATT CTT GCT CTT CCG CAG GTC AAG GCC GTT GTC TGG GCG GGT CTT    1988
Gln Ile Leu Ala Leu Pro Gln Val Lys Ala Val Val Trp Ala Gly Leu
                525                 530                 535

CCT TCT CAG GAG AGC GGC AAT GCG CTC GTC GAC GTG CTG TGG GGA GAT    2036
Pro Ser Gln Glu Ser Gly Asn Ala Leu Val Asp Val Leu Trp Gly Asp
                540                 545                 550

GTC AGC CCT TCT GGC AAG CTG GTG TAC ACC ATT GCG AAG AGC CCC AAT    2084
Val Ser Pro Ser Gly Lys Leu Val Tyr Thr Ile Ala Lys Ser Pro Asn
                555                 560                 565

GAC TAT AAC ACT CGC ATC GTT TCC GGC GGC AGT GAC AGC TTC AGC GAG    2132
Asp Tyr Asn Thr Arg Ile Val Ser Gly Gly Ser Asp Ser Phe Ser Glu
    570                 575                 580

GGA CTG TTC ATC GAC TAT AAG CAC TTC GAC GAC GCC AAT ATC ACG CCG    2180
Gly Leu Phe Ile Asp Tyr Lys His Phe Asp Asp Ala Asn Ile Thr Pro
585                 590                 595                 600

CGG TAC GAG TTC GGC TAT GGA CTG  T GTAAGTTTGC TAACCTGAAC           2225
Arg Tyr Glu Phe Gly Tyr Gly Leu
                605

AATCTATTAG ACAGGTTGAC TGACGGATGA CTGTGGAATG ATAG  CT TAC ACC AAG   2280
                                                  Ser Tyr Thr Lys
                                                              610

TTC AAC TAC TCA CGC CTC TCC GTC TTG TCG ACC GCC AAG TCT GGT CCT    2328
Phe Asn Tyr Ser Arg Leu Ser Val Leu Ser Thr Ala Lys Ser Gly Pro
                615                 620                 625

GCG ACT GGG GCC GTT GTG CCG GGA GGC CCG AGT GAT CTG TTC CAG AAT    2376
Ala Thr Gly Ala Val Val Pro Gly Gly Pro Ser Asp Leu Phe Gln Asn
                630                 635                 640

GTC GCG ACA GTC ACC GTT GAC ATC GCA AAC TCT GGC CAA GTG ACT GGT    2424
Val Ala Thr Val Thr Val Asp Ile Ala Asn Ser Gly Gln Val Thr Gly
645                 650                 655                 660

GCC GAG GTA GCC CAG CTG TAC ATC ACC TAC CCA TCT TCA GCA CCC AGG    2472
Ala Glu Val Ala Gln Leu Tyr Ile Thr Tyr Pro Ser Ser Ala Pro Arg
                665                 670                 675

ACC CCT CCG AAG CAG CTG CGA GGC TTT GCC AAG CTG AAC CTC ACG CCT    2520
Thr Pro Pro Lys Gln Leu Arg Gly Phe Ala Lys Leu Asn Leu Thr Pro
                680                 685                 690

GGT CAG AGC GGA ACA GCA ACG TTC AAC ATC CGA CGA CGA GAT CTC AGC    2568
Gly Gln Ser Gly Thr Ala Thr Phe Asn Ile Arg Arg Arg Asp Leu Ser
                695                 700                 705

TAC TGG GAC ACG GCT TCG CAG AAA TGG GTG GTG CCG TCG GGG TCG TTT    2616
Tyr Trp Asp Thr Ala Ser Gln Lys Trp Val Val Pro Ser Gly Ser Phe
    710                 715                 720

GGC ATC AGC GTG GGA GCG AGC AGC CGG GAT ATC AGG CTG ACG AGC ACT    2664
Gly Ile Ser Val Gly Ala Ser Ser Arg Asp Ile Arg Leu Thr Ser Thr
725                 730                 735                 740

CTG TCG GTA GCG TAGCGCGAGG AGGGTGAAGG CGGTTGACCT GTGACTGTGA        2716
Leu Ser Val Ala
            745

GTGAGGACCG AAGGTGGGAT GGCGTGAATA CTGCAGGAAT ACAATCTTCA GGATAGGCAT  2776

CAGAGCAGTA ACATGAATGA TGAAGACGGC CGAAGCAGAA GTGAATTGAG GAGGTAGTGA  2836

TGATGAAATG TGAGGGAAGA GAGATGTTCA ATCACCTTGT TCGAGGGAAG CTGCAAATTG  2896

GGCCTCACGT CATCTCGCAG AGAGAAGGAA CTCTTGCAGC AGGAGTTCTG CTCACTGAGA  2956

AGAAGGCCCG GGTTAGCGTC GCGCCTCTTC CGCGACATCC TCCGCTCCGG CACTGTGCTG  3016

TCAAACTGGC ACCAACA                                                 3033
```

(2) INFORMATION FOR SEQ ID NO:2:

(i) SEQUENCE CHARACTERISTICS:
        (A) LENGTH: 744 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Tyr Arg Thr Ala Ala Leu Ala Leu Ala Thr Gly Pro Phe
 1               5                  10                  15

Ala Arg Ala Asp Ser His Ser Thr Ser Gly Ala Ser Ala Glu Ala Val
            20                  25                  30

Val Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
        50                  55                  60

Gly Val Gly Trp Asn Gly Gly Pro Cys Val Gly Asn Thr Ser Pro Ala
 65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
```

```
                355                 360                 365
Ala Asn Ile Leu Pro Leu Lys Lys Pro Ala Ser Ile Ala Val Val Gly
        370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
                420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
        450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
        595                 600                 605

Ser Tyr Thr Lys Phe Asn Tyr Ser Arg Leu Ser Val Leu Ser Thr Ala
610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
        675                 680                 685

Asn Leu Thr Pro Gly Gln Ser Gly Thr Ala Thr Phe Asn Ile Arg Arg
690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

(2) INFORMATION FOR SEQ ID NO:3:

(i) SEQUENCE CHARACTERISTICS:
        (A) LENGTH: 14 base pairs
```

```
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: modified_base
            (B) LOCATION: 3
            (D) OTHER INFORMATION: /mod_base= i
                /label= n (ix) FEATURE:
            (A) NAME/KEY: modified_base
            (B) LOCATION: 6
            (D) OTHER INFORMATION: /mod_base= i
                /label= n (ix) FEATURE:
            (A) NAME/KEY: modified_base
            (B) LOCATION: 12
            (D) OTHER INFORMATION: /mod_base= i
                /label= n (xi) SEQUENCE DESCRIPTION: SEQ ID NO:3:

GCNGTNCCTG CNGG                                                               14

(2) INFORMATION FOR SEQ ID NO:4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: modified_base
            (B) LOCATION: 7
            (D) OTHER INFORMATION: /mod_base= i (xi) SEQUENCE DESCRIPTION: SEQ ID NO:4:

GTTRTTNCCR TTRAARTCTG T                                                       21
```